(12) United States Patent
Choi et al.

(10) Patent No.: US 11,560,416 B2
(45) Date of Patent: Jan. 24, 2023

(54) METHOD FOR PRODUCING DUAL FUNCTION PROTEINS AND ITS DERIVATIVES

(71) Applicant: YUHAN CORPORATION, Seoul (KR)

(72) Inventors: Byung Hyun Choi, Suwon-si (KR); In Hwan Lim, Suwon-si (KR); Jun Young Park, Seoul (KR); Jin Hyoung Lee, Yongin-si (KR); Ki Hong Kim, Suwon-si (KR); Hae Yong Jo, Seoul (KR); Jun Hwan Kim, Seoul (KR); Moo Young Song, Suwon-si (KR); Jong Gyun Kim, Anyang-si (KR)

(73) Assignee: YUHAN CORPORATION, Seoul (KR)

( * ) Notice: Subject to any disclaimer, the term of this patent is extended or adjusted under 35 U.S.C. 154(b) by 155 days.

(21) Appl. No.: 16/606,279

(22) PCT Filed: Apr. 20, 2018

(86) PCT No.: PCT/KR2018/004599
§ 371 (c)(1),
(2) Date: Oct. 18, 2019

(87) PCT Pub. No.: WO2018/194413
PCT Pub. Date: Oct. 25, 2018

(65) Prior Publication Data
US 2021/0188936 A1 Jun. 24, 2021

(30) Foreign Application Priority Data
Apr. 21, 2017 (KR) ........................ 10-2017-0051758

(51) Int. Cl.
| | |
|---|---|
| *C12N 15/62* | (2006.01) |
| *C12N 15/09* | (2006.01) |
| *C12N 5/00* | (2006.01) |
| *C07K 16/46* | (2006.01) |
| *C07K 19/00* | (2006.01) |
| *C07K 14/605* | (2006.01) |
| *C07K 14/50* | (2006.01) |
| *C12P 21/02* | (2006.01) |
| *C12N 15/00* | (2006.01) |

(52) U.S. Cl.
CPC ............ *C07K 14/605* (2013.01); *C07K 14/50* (2013.01); *C12P 21/02* (2013.01); *C07K 16/46* (2013.01); *C07K 19/00* (2013.01); *C07K 2319/30* (2013.01); *C12N 5/00* (2013.01); *C12N 15/00* (2013.01)

(58) Field of Classification Search
None
See application file for complete search history.

(56) References Cited

U.S. PATENT DOCUMENTS

| | | | |
|---|---|---|---|
| 5,851,800 | A | 12/1998 | Adamson et al. |
| 9,023,791 | B2 | 5/2015 | Boettcher et al. |
| 9,434,778 | B2 | 9/2016 | Morin et al. |
| 9,441,030 | B2 | 9/2016 | Song et al. |
| 9,926,351 | B2 | 3/2018 | Schellenberger et al. |
| 2010/0112641 | A1* | 5/2010 | Song .................. C07K 1/22 435/69.6 |
| 2011/0034373 | A1 | 2/2011 | Coskun et al. |
| 2011/0195895 | A1 | 8/2011 | Walker et al. |
| 2012/0035099 | A1 | 2/2012 | Garibay et al. |
| 2012/0172298 | A1 | 7/2012 | Andersen et al. |
| 2012/0238496 | A1 | 9/2012 | Fan et al. |
| 2013/0129724 | A1 | 5/2013 | Boettcher et al. |
| 2013/0190232 | A1 | 7/2013 | Tagmose et al. |
| 2014/0073563 | A1 | 3/2014 | Boscheinen et al. |
| 2014/0213512 | A1 | 7/2014 | Ellison et al. |
| 2014/0243503 | A1 | 8/2014 | Belouski et al. |
| 2014/0323396 | A1* | 10/2014 | Belouski ............... A61P 3/00 514/5.1 |
| 2018/0298078 | A1 | 10/2018 | Park et al. |
| 2018/0305428 | A1 | 10/2018 | Kim et al. |
| 2019/0314452 | A1 | 10/2019 | Hong et al. |
| 2020/0024318 | A1 | 1/2020 | Kim et al. |

FOREIGN PATENT DOCUMENTS

| | | |
|---|---|---|
| CN | 101993496 A | 3/2011 |
| CN | 102558358 A | 7/2012 |
| CN | 102625811 A | 8/2012 |
| CN | 102655877 A | 9/2012 |
| CN | 102802657 A | 11/2012 |
| CN | 103124562 A | 5/2013 |

(Continued)

OTHER PUBLICATIONS

Bedoya-López et al. Effect of Temperature Downshift on the Transcriptomic Responses of Chinese Hamster Ovary Cells Using Recombinant Human Tissue Plasminogen Activator Production Culture. PLoS One 11(3): e0151529, pp. 1-26 (Mar. 18, 2016). (Year: 2016).*

Alexei Kharitonenkov et al., "FGF-21 as a novel metabolic regulator", The Journal of Clinical Investigation, Jun. 2005, pp. 1627-1635, vol. 115, No. 6.

Bernard Thorens et al., "Cloning and Functional Expression of the Human Islet GLP-1 Receptor," Diabetes, Nov. 1993, pp. 1678-1682, vol. 42.

H. Kahal et al., "Glucagon-like peptide-1 analogue, liraglutide, improves liver fibrosis markers in obese women with polycystic ovary syndrome and nonalcoholic fatty liver disease", Clinical Endocrinology, 2014, pp. 523-528, vol. 81.

(Continued)

*Primary Examiner* — Elizabeth C. Kemmerer
*Assistant Examiner* — Regina M DeBerry
(74) *Attorney, Agent, or Firm* — Sughrue Mion, PLLC

(57) ABSTRACT

A method for producing a dual function protein includes a biologically active protein and an FGF21 mutant protein. The method allows stable production of a target protein by effectively preventing decomposition of the target protein, and thus has a high potential for commercial usage.

8 Claims, 5 Drawing Sheets

Specification includes a Sequence Listing.

(56) References Cited

FOREIGN PATENT DOCUMENTS

| | | | |
|---|---|---|---|
| CN | 103415300 A | 11/2013 |
| CN | 104736558 A | 6/2015 |
| CN | 105288592 A | 2/2016 |
| EA | 020843 B1 | 2/2015 |
| EP | 0 306 968 A2 | 3/1989 |
| EP | 0 345 660 A1 | 12/1989 |
| EP | 2 548 570 A1 | 1/2013 |
| JP | 2006-520186 A | 9/2006 |
| JP | 2009-534424 A | 9/2009 |
| JP | 2010-531134 A | 9/2010 |
| JP | 2011-518175 A | 6/2011 |
| JP | 2011-523561 A | 8/2011 |
| JP | 2012-504965 A | 3/2012 |
| JP | 2012-515747 A | 7/2012 |
| JP | 2012-525847 A | 10/2012 |
| JP | 2014-510707 A | 5/2014 |
| JP | 2014-526441 A | 10/2014 |
| JP | 2014-527986 A | 10/2014 |
| JP | 2015-527974 A | 9/2015 |
| JP | 2018-522147 A | 8/2018 |
| JP | 2018-534929 A | 11/2018 |
| JP | 2019-500013 A | 1/2019 |
| JP | 2020-502053 A | 1/2020 |
| RU | 2 741 345 C2 | 1/2021 |
| WO | 90/02175 A1 | 3/1990 |
| WO | 2003/011213 A2 | 2/2003 |
| WO | 03/059934 A2 | 7/2003 |
| WO | 2004/058800 A2 | 7/2004 |
| WO | 2005/000892 A2 | 1/2005 |
| WO | 2005/091944 A2 | 10/2005 |
| WO | 2007/124463 A1 | 11/2007 |
| WO | 2008/147143 A2 | 12/2008 |
| WO | 2009/020802 A2 | 2/2009 |
| WO | 2009/129379 A1 | 10/2009 |
| WO | 2009/149171 A2 | 12/2009 |
| WO | 2010/042747 A2 | 4/2010 |
| WO | 2010/065439 A1 | 6/2010 |
| WO | 2010/084169 A2 | 7/2010 |
| WO | 2010/091122 A1 | 8/2010 |
| WO | 2010/129503 A1 | 11/2010 |
| WO | 2010/129600 A2 | 11/2010 |
| WO | 2010/142665 A1 | 12/2010 |
| WO | 2011/020319 A1 | 2/2011 |
| WO | 2011/028229 A1 | 3/2011 |
| WO | 2011/089170 A2 | 7/2011 |
| WO | 2011/154349 A2 | 12/2011 |
| WO | 2012/010553 A1 | 1/2012 |
| WO | 2012/066075 A1 | 5/2012 |
| WO | 2012/093127 A2 | 7/2012 |
| WO | 2012/170438 A2 | 12/2012 |
| WO | 2013/033452 A2 | 3/2013 |
| WO | 2013/049234 A2 | 4/2013 |
| WO | 2013/131091 A1 | 9/2013 |
| WO | 2013/188181 A1 | 12/2013 |
| WO | 2014/037373 A1 | 3/2014 |
| WO | 2014/130659 A1 | 8/2014 |
| WO | 2015/038938 A1 | 3/2015 |
| WO | 2017/065559 A1 | 4/2017 |
| WO | 2017/074117 A1 | 5/2017 |
| WO | 2017/074123 A1 | 5/2017 |
| WO | 2018/088838 A1 | 5/2018 |
| WO | 2018/166461 A1 | 9/2018 |
| WO | 2018/194413 A1 | 10/2018 |

OTHER PUBLICATIONS

Hecht et al., "Rationale-Based Engineering of a Potent Long-Acting FGF21 Analog for the Treatment of Type 2 Diabetes", PLOS One, Nov. 2012, vol. 7, Issue 11, e49345, pp. 1-14 (total 14 pages).

Jie Huang et al., "Development of a Novel Long-Acting Antidiabetic FGF21 Mimetic by Targeted Conjugation to a Scaffold Antibody", The Journal of Pharmacology and Experimental Therapeutics, Aug. 2013, pp. 270-280, vol. 346.

Justin D. Schumacher et al., "Regulation of Hepatic Stellate Cells and Fibrogenesis by Fibroblast Growth Factors", BioMed Research International, Jan. 2016 (Posted on ResearchGate), 21 pages.

English Translation of Office Action dated Jan. 28, 2021 in Russian Application No. 2019117767.

International Search Report of PCT/KR2018/004599 dated Aug. 21, 2018 [PCT/ISA/210].

Written Opinion of PCT/KR2018/004599 dated Aug. 21, 2018 [PCT/ISA/237].

Michelle Orlando, "Modification of proteins and low molecular weight substances with hydroxyethyl starch (HES)", 2003, Inauguraldissertation, Giesen (191 pages).

Richard Smith et al., "FGF21 Can Be Mimicked In Vitro and In Vivo by a Novel Anti-FGFR1c/β-Klotho Bispecific Protein", PLOS One, 2013, vol. 8, Issue 4, e61432 (11 pages total).

Xiaoying Chen et al., "Fusion Protein Linkers: Property, Design and Functionality", Adv Drug Deliv Rev., 2013, vol. 65, No. 10, pp. 1357-1369 (32 pages total).

Joel D.A. Tyndall et al., "Over One Hundred Peptide-Activated G Protein-Coupled Receptors Recognize Ligands with Turn Structure", Chem. Rev., 2005, vol. 105, No. 3, pp. 793-826 (34 pages total).

Yumi Maeda et al., "Engineering of Functional Chimeric Protein G-Vargula Luciferase", Analytical Biochemistry, 1997, vol. 249, No. 2, pp. 147-152 (6 pages total).

H-D. Jakubke et al., "I am amino acids, peptides, proteins: Per-M: Mir", 1985 (5 pages total).

H.N. Hong et al., "YH25724, a novel long-acting GLP-1/FGF21 dual agonist lowers both non-alcoholic fatty liver disease activity score and fibrosis stage in a diet-induced obese mouse model of biopsy-confirmed non-alcoholic steatohepatitis", Journal of Hepatology, vol. 66; pp. S16-S17; published 2017.

Wolfgang Glaesner et al., "Engineering and characterization of the long-acting glucagon-like peptide-1 analogue LY2189265, an Fc fusion protein", Diabetes/Metabolism Research and Reviews, V. 26, N. 4, p. 287-296; published Apr. 30, 2010.

Tokuriki et al., "Stability effects of mutations and protein evolvability", Current Opinion in Structural Biology, v.19, n.5, p. 596-604; published 2009.

Shen et al., "Single Variable Domain-IgG Fusion: A Novel Recombinant Approach to Fc Domain-Containing Bispecific Antibodies", Journal of Biological Chemistry, V. 281, N. 16, p. 10706-10714; published Apr. 21, 2006.

N.E. Kuzmina et al., "Quantitative Determination of the Mean Molecular Mass of Dextrans by Means of Diffusion-Ordered NMR Spectroscopy", Journal of Analytical Chemistry, vol. 69, No. 10, pp. 1047-1053; published 2014.

Neidigh et al., "Exendin-4 and Glucagon-like-peptide-1: NMR Structural Comparisons in the Solution and Micelle-Associated States", Biochemistry, vol. 40, No. 44, pp. 13188-13200; published Oct. 13, 2001.

\* cited by examiner

[Fig. 1]
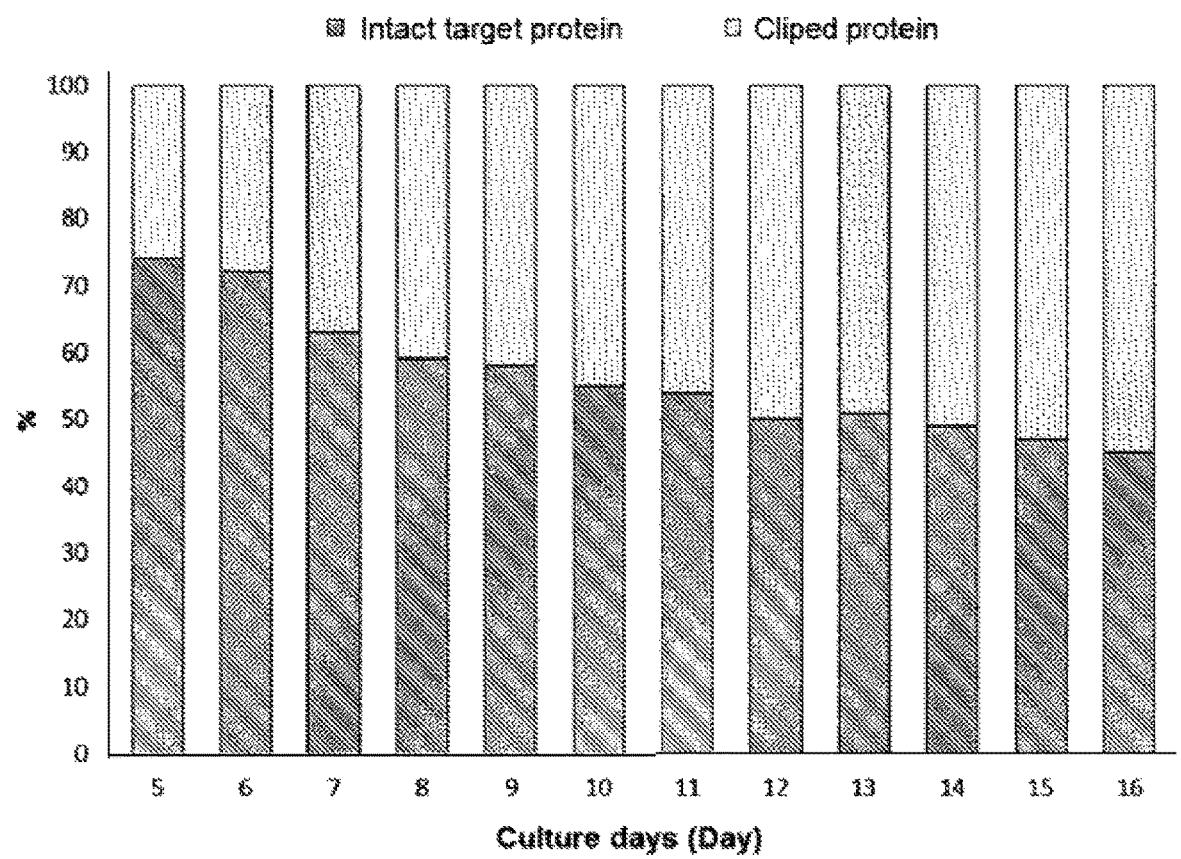
[Fig. 2]
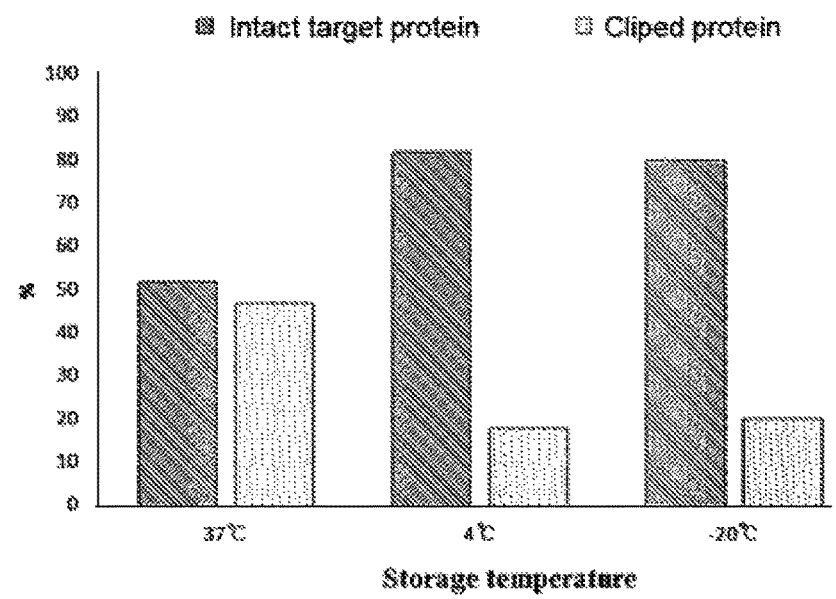

[Fig. 3]
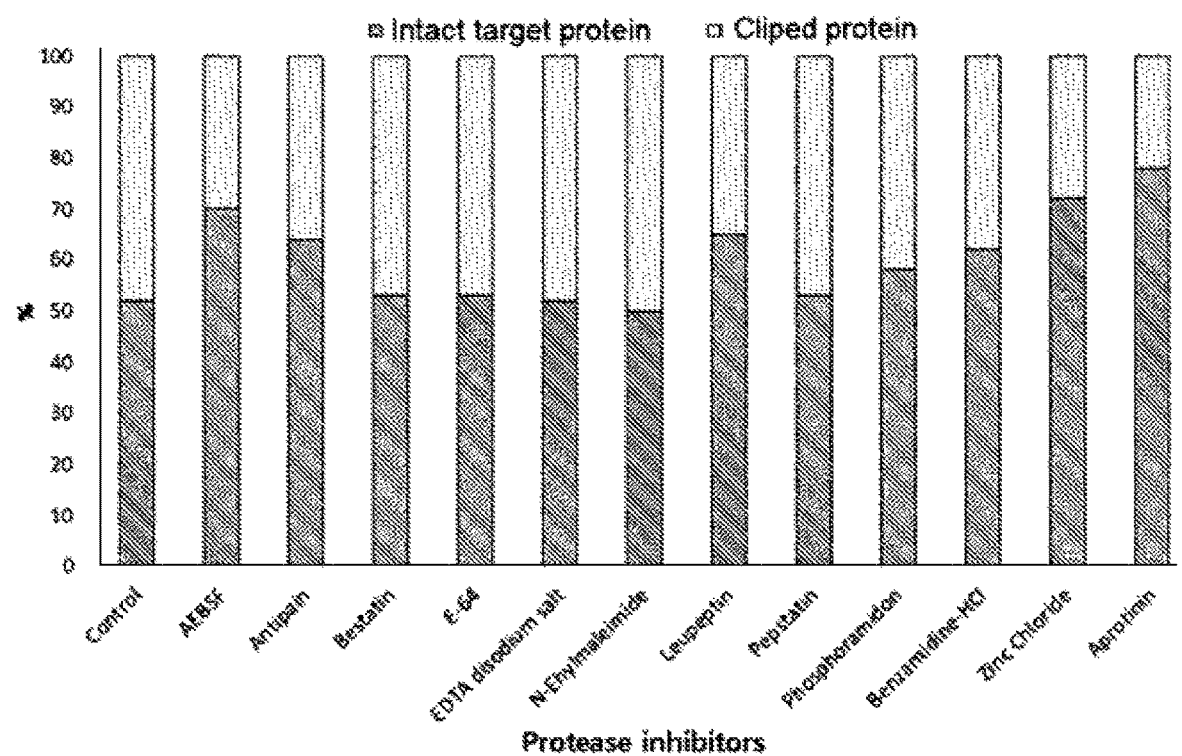

[Fig. 4]
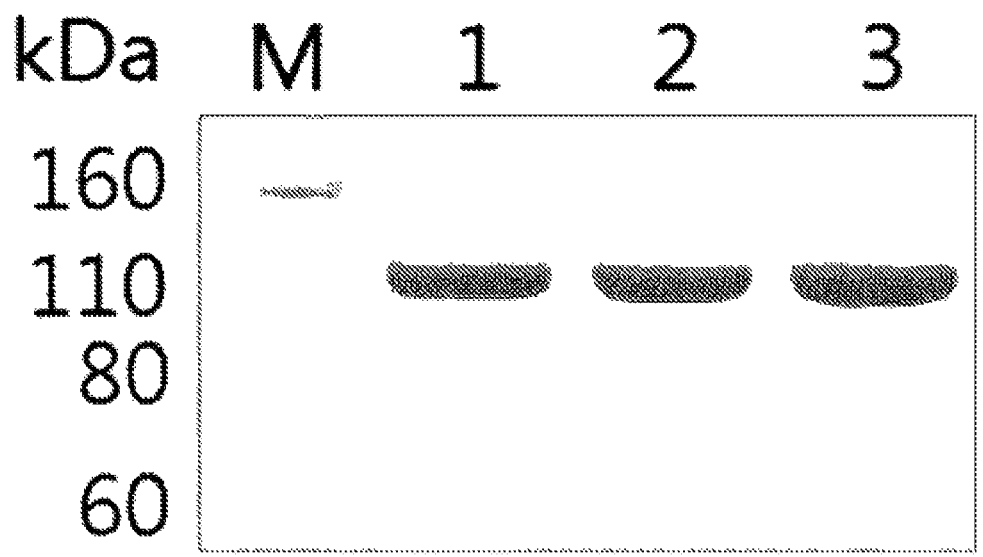
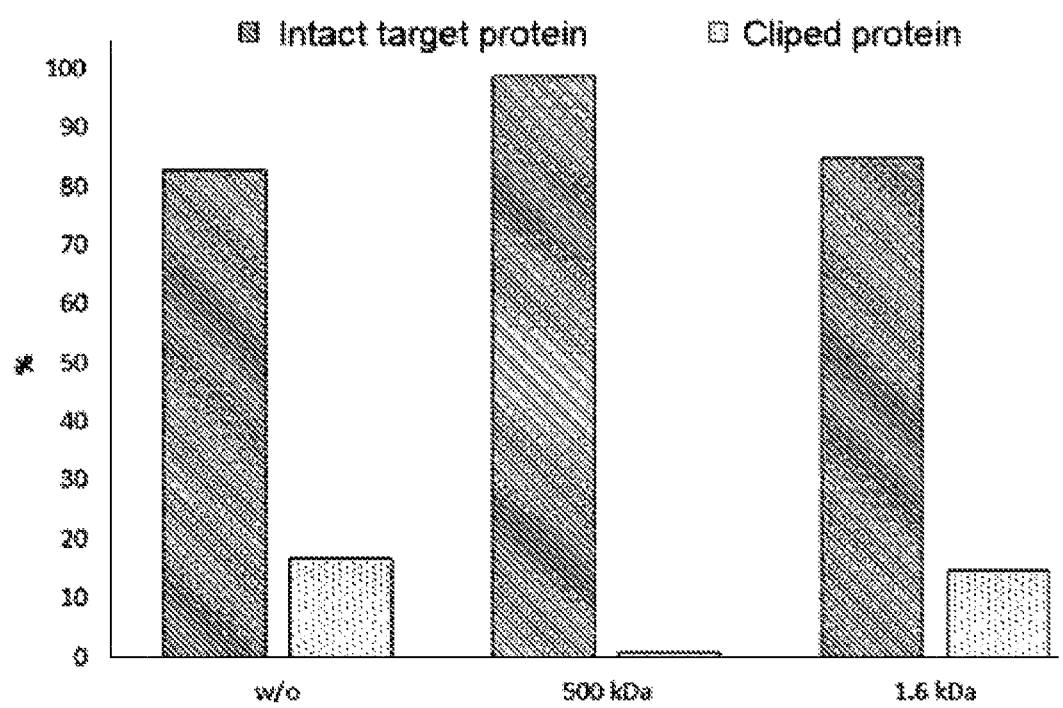

[Fig. 5]
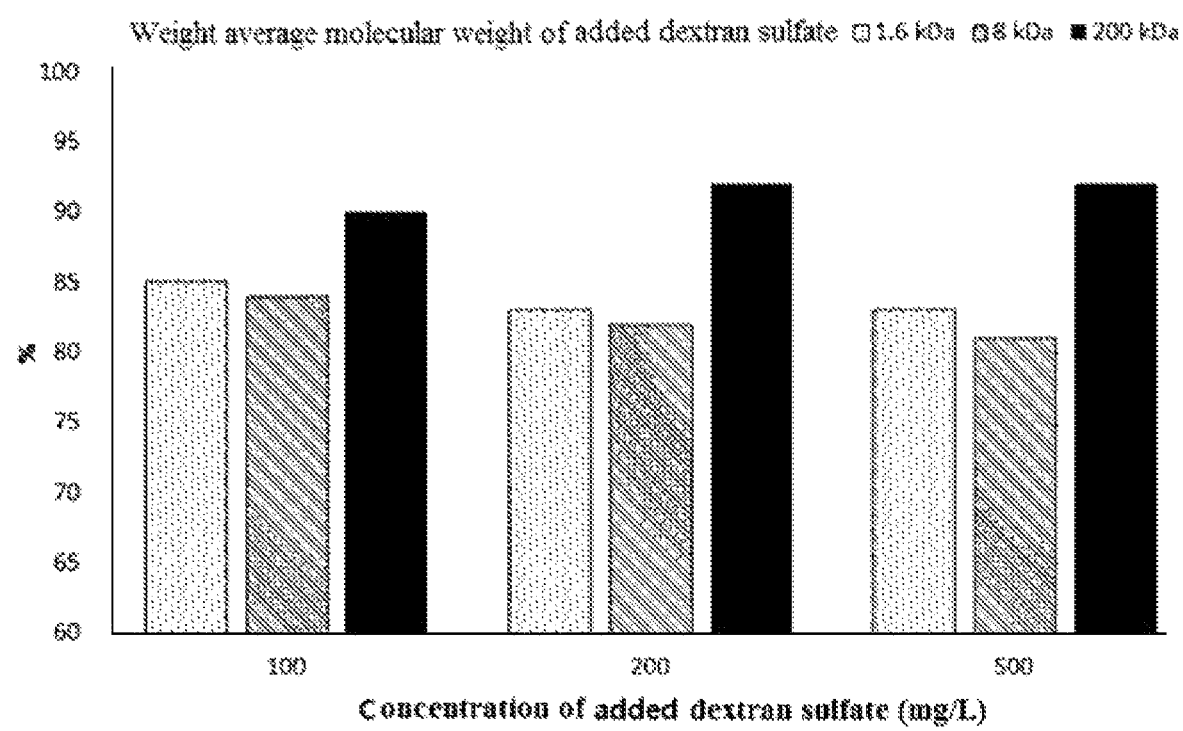

[Fig. 6]
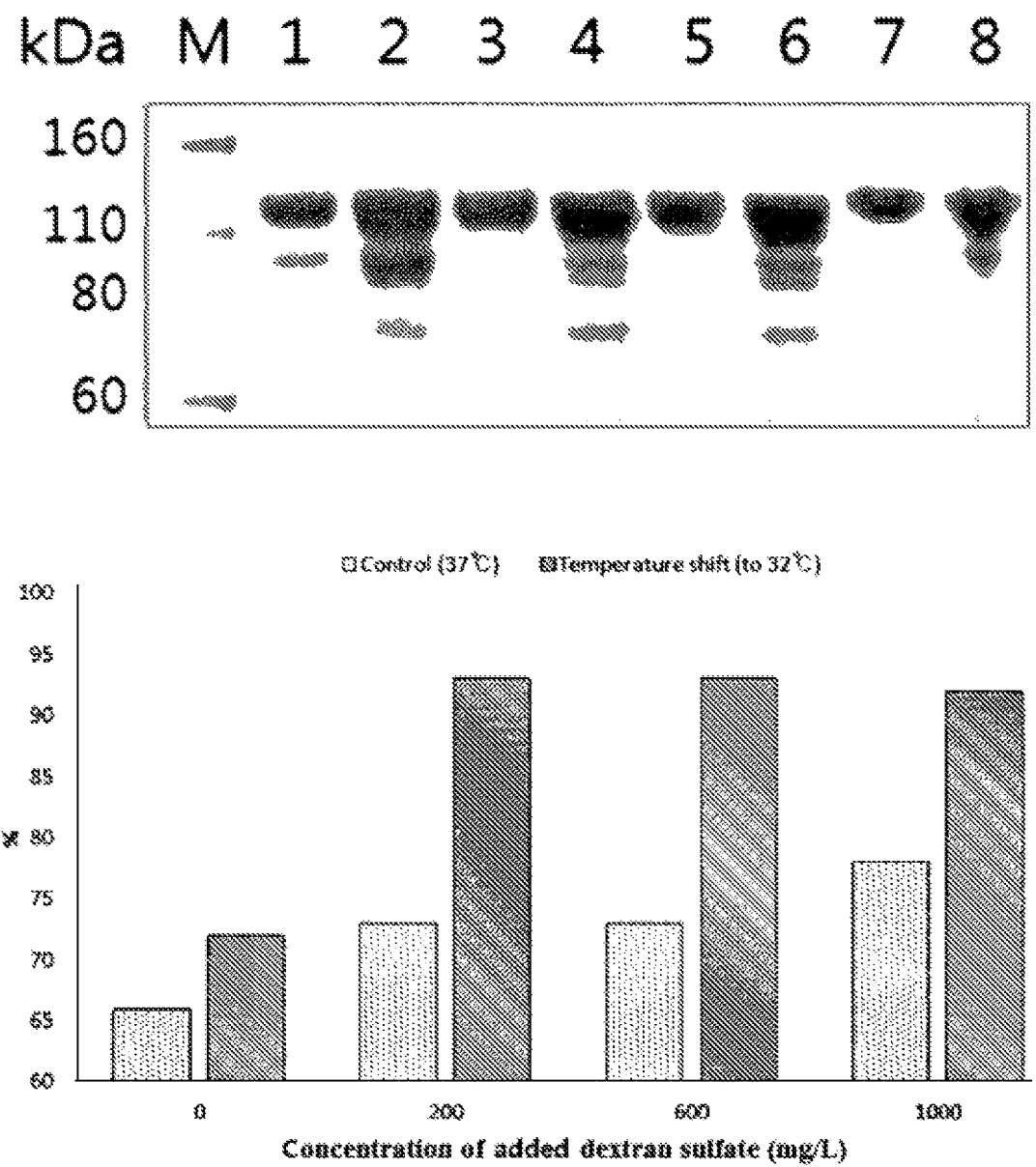

METHOD FOR PRODUCING DUAL FUNCTION PROTEINS AND ITS DERIVATIVES

CROSS REFERENCE TO RELATED APPLICATIONS

This application is a National Stage of International Application No. PCT/KR2018/004599, filed Apr. 20, 2018, claiming priority to Korean Patent Application No. 10-2017-0051758, filed Apr. 21, 2017.

TECHNICAL FIELD

The present invention relates to a method for producing a dual function protein comprising a biologically active protein and a fibroblast growth factor 21 (an FGF21) mutant protein.

BACKGROUND ART

When an animal cell is used to produce a recombinant protein, there might be a problem that a specific region of the target protein may be clipped by a protease is secreted by an animal cell (host cell) to cause heterogeneity, reduction or inactivation of the recombinant protein. In addition, such clipping of the expressed protein also leads to the problem that it gets difficult to maintain "lot to lot" homogeneity during production and purification processes. For this reason, it is necessary to keep the protease at a low level or suppress the protease activity during the production of a recombinant protein.

As an alternative to solve the problem, a production method in which inhibitors against serine, cysteine, aspartic acid or aminopeptidase (such as aprotinin, bestatin, leupeptin, E-64 and pepstatin A, etc.) are added in the culture medium was proposed (see WO 1990-002175, EP 0,306,968, and U.S. Pat. No. 5,851,800). However, the use of these inhibitors in commercial production is not effective because of cytotoxicity and the need for extra efforts to prove that they have been completely removed from the final product. In addition, among conventional alternatives, a universal method applicable to all target proteins produced in host cells has not been found yet.

DISCLOSURE OF INVENTION

Technical Problem

It is an object of the present invention to provide a culture method for producing a dual function protein comprising a biologically active protein and an FGF21 mutant protein, which has improved pharmacokinetic parameters, high stability, less potential for aggregation to form a complex, and less immunogenic potential.

Solution to Problem

In accordance with one object of the present invention, there is provided a method for producing a recombinant dual function protein from a mammalian host cell transformed with an expression vector containing cDNA encoding a dual function protein or a derivative thereof, the method comprising culturing the mammalian host cell in a culture medium supplemented with dextran sulfate, wherein the dual function protein comprises a fibroblast growth factor 21 (FGF21) mutant protein; a biologically active protein, or a mutant or fragment thereof; and an Fc region of an immunoglobulin, wherein the FGF21 mutant protein comprises at least one mutation selected from the group consisting of the mutations (1) to (7) below:

(1) a substitution of amino acids at positions 98 to 101 from the N-terminus of a wild-type FGF21 protein with an amino acid sequence of EIRP (SEQ ID NO: 53);

(2) a substitution of amino acids at positions 170 to 174 from the N-terminus of a wild-type FGF21 protein with an amino acid sequence of TGLEAV (SEQ ID NO: 54);

(3) a substitution of amino acids at positions 170 to 174 from the N-terminus of a wild-type FGF21 protein with an amino acid sequence of TGLEAN (SEQ ID NO: 55);

(4) a substitution of an amino acid at position 170 from the N-terminus of a wild-type FGF21 protein with an amino acid N;

(5) a substitution of an amino acid at position 174 from the N-terminus of a wild-type FGF21 protein with an amino acid N;

(6) a substitution of an amino acid at position 180 from the N-terminus of a wild-type FGF21 protein with an amino acid E, along with one or more mutations (1) to (5) above; and (7) a mutation of 1 to 10 amino acids for reducing immunogenicity of a wild-type FGF21 protein.

Advantageous Effects of Invention

The production method of the present invention allows stable production of a target protein by effectively preventing decomposition of the target protein.

BRIEF DESCRIPTION OF DRAWINGS

FIG. 1 is a schematic diagram showing the result of analysis of the culture supernatant by SDS-PAGE after suspension culture of a cell line expressing a dual function protein. It was found that as the culture time elapsed, other proteins smaller than the non-clipped dual function protein were expressed together.

FIG. 2 is a schematic diagram showing the result of analysis of the culture supernatant by SDS-PAGE according to storage temperature conditions after a certain time period. The culture supernatant stored at 4° C. or −20° C. showed reduced clipping of the dual function proteins as compared to that stored at 37° C. This result indicated that the clipping phenomenon of the dual function proteins was induced by the protease derived from the host cell.

FIG. 3 is a schematic diagram showing the result of analysis by SDS-PAGE after adding protease inhibitors to the culture supernatants and storing the mixtures for a certain time period at 37° C. It was found that mainly the addition of serine protease inhibitor decreased the clipping phenomenon of the dual function protein. This result indicated that the clipping phenomenon of the dual function protein was induced by the protease derived from the host cell.

FIG. 4 is the result of analysis of the culture supernatant by SDS-PAGE after a cell culture in which dextran sulfate was added to the culture medium, and the graph thereof. The effect of reducing the clipping phenomenon of the dual function protein was not observed when dextran sulfate having a weight average molecular weight of 1.6 kDa was added, whereas clipping phenomenon of the dual function protein was reduced when 500 kDa dextran sulfate was added.

FIG. 5 is a schematic diagram showing the result of analysis of the culture supernatant by SDS-PAGE after culturing with dextran sulfates having different weight average molecular weights added to the culture medium. When dextran sulfate having a weight average molecular weight of 200 kDa or more was added to the culture medium, the clipping phenomenon of the dual function protein was reduced.

FIG. 6 is the result of SDS-PAGE analysis of the culture supernatant after the culture in which dextran sulfates at various concentrations were added to the culture medium, and the graph thereof. When dextran sulfate was added at 200-1,000 mg/L, the clipping phenomenon of the dual function protein was reduced. In addition, when the culture temperature was changed to 32° C. during the culture, the clipping phenomenon of the dual function protein could be prevented more effectively.

BEST MODE FOR CARRYING OUT THE INVENTION

In accordance with one object of the present invention, there is provided a method for producing a recombinant dual function protein from a mammalian host cell transformed with an expression vector containing cDNA encoding a dual function protein or a derivative thereof, the method comprising culturing the mammalian host cell in a culture medium supplemented with dextran sulfate, wherein the dual function protein comprises a fibroblast growth factor 21 (FGF21) mutant protein; a biologically active protein, or a mutant or fragment thereof; and an Fc region of an immunoglobulin, wherein the FGF21 mutant protein comprises at least one mutation selected from the group consisting of the mutations (1) to (7) below:

(1) a substitution of amino acids at positions 98 to 101 from the N-terminus of a wild-type FGF21 protein with an amino acid sequence of EIRP (SEQ ID NO: 53) (hereinafter, "EIRP");

(2) a substitution of amino acids at positions 170 to 174 from the N-terminus of a wild-type FGF21 protein with an amino acid sequence of TGLEAV (SEQ ID NO: 54) (hereinafter, "TGLEAV");

(3) a substitution of amino acids at positions 170 to 174 from the N-terminus of a wild-type FGF21 protein with an amino acid sequence of TGLEAN (SEQ ID NO: 55) (hereinafter, "TGLEAN");

(4) a substitution of an amino acid at position 170 from the N-terminus of a wild-type FGF21 protein with an amino acid N (hereinafter, "G170N");

(5) a substitution of an amino acid at position 174 from the N-terminus of a wild-type FGF21 protein with an amino acid N (hereinafter, "G174N");

(6) a substitution of an amino acid at position 180 from the N-terminus of a wild-type FGF21 protein with an amino acid E, along with one or more mutations (1) to (5) above (hereinafter, "A180E"); and (7) a mutation of 1 to 10 amino acids for reducing immunogenicity of a wild-type FGF21 protein.

FGF21 Mutant Protein

The wild-type FGF21 protein, a hormone known to play an important role in glucose and lipid homeostasis, may be one derived from mammals such as humans, mice, pigs, monkeys, etc., preferably from humans. More preferably, the wild-type FGF21 protein may be the wild-type human FGF21 protein having an amino acid sequence represented by SEQ ID NO: 1.

Preferably, the mutation included in the FGF21 mutant proteins may be any one of the mutations of EIRP(SEQ ID NO: 53), TGLEAV(SEQ ID NO: 54), TGLEAN(SEQ ID NO: 55), G170N and G174N; a combination of any one of the mutations of TGLEAV(SEQ ID NO: 54), TGLEAN (SEQ ID NO: 55), G170N and G174N and the mutation of EIRP(SEQ ID NO: 53); a combination of any one of the mutations of EIRP(SEQ ID NO: 53), TGLEAV(SEQ ID NO: 54), TGLEAN(SEQ ID NO: 55), G170N and G174N and the mutation of A180E; or a combination of any one of the mutations of TGLEAV(SEQ ID NO: 54), TGLEAN(SEQ ID NO: 55), G170N and G174N, the mutation of EIRP and the mutation of A180E.

The EIRP(SEQ ID NO: 53) refers to a mutation in which LLLE(SEQ ID NO: 57), the amino acids at positions 98 to 101 from the N terminus of a wild-type FGF21 protein, is substituted with EIRP(SEQ ID NO: 53). Further, the TGLEAV(SEQ ID NO: 54) refers to a mutation in which GPSQG(SEQ ID NO: 58), the amino acids at positions 170 to 174 from the N terminus of a wild-type FGF21 protein, is substituted with TGLEAV(SEQ ID NO: 54). In addition, the TGLEAN(SEQ ID NO: 55) refers to a mutation in which GPSQG(SEQ ID NO: 58), the amino acids at positions 170 to 174 from the N terminus of a wild-type FGF21 protein, is substituted with TGLEAN(SEQ ID NO: 55). Further, the G170N refers to a mutation in which G, the amino acid at position 170 from the N terminus of a wild-type FGF21 protein, is substituted with N. In addition, the G174N refers to a mutation in which G, the amino acid at position 174 from the N terminus of a wild-type FGF21 protein, is substituted with N.

Furthermore, the FGF21 mutant proteins may have a conformation, in which 1 to 10 amino acids at the N-terminus or C-terminus is (are) deleted as compared to the wild-type FGF21 protein. More preferably, the FGF21 mutant proteins may include an amino acid sequence represented by any one of SEQ ID NOs: 6 to 23. Still more preferably, the FGF21 mutant proteins may include an amino acid sequence represented by any one of SEQ ID NOs: 6 to 23 and further have a conformation, in which 1 to 10 amino acids at the N-terminus or C-terminus is (are) deleted as compared to the wild-type FGF21 protein.

In the dual function protein, an amino acid residue N of FGF21 mutant protein introduced by a mutation may be glycosylated.

Biologically Active Protein

The biologically active protein may be one selected from the group consisting of insulin, C-peptide, leptin, glucagon, gastrin, gastric inhibitory polypeptide (GIP), amylin, calcitonin, cholecystokinin, peptide YY, neuropeptide Y, bone morphogenetic protein-6 (BMP-6), bone morphogenetic protein-9 (BMP-9), oxyntomodulin, oxytocin, glucagon-like peptide-1 (GLP-1), glucagon-like peptide-2 (GLP-2), irisin, fibronectin type III domain-containing protein 5 (FNDC5), apelin, adiponectin, C1q and tumor necrosis factor related protein (CTRP family), resistin, visfatin, omentin, retinol binding protein-4 (RBP-4), glicentin, angiopoietin, interleukin-22 (IL-22), exendin-4 and growth hormone. Preferably, the biologically active protein may be one selected from GLP-1, a mutant thereof and exendin-4.

The GLP-1 protein is an incretin hormone consisting of 31 amino acids, which is to secreted by L cells in the intestinal tract stimulated by food, etc. For example, the GLP-1 protein may be represented by the amino acid sequence of SEQ ID NO: 29.

A mutant of GLP-1 may be represented, for example, by the amino acid sequence of any one of SEQ ID NOs: 30 to 33.

Fc Region of Immunoglobulin

As used herein, the term "Fc region," "Fc fragment," or "Fc" refers to a protein, which includes a heavy chain constant region 1 (CH1), a heavy chain constant region 2 (CH2) and a heavy chain constant region 3 (CH3) of an immunoglobulin, but does not include variable regions of the heavy and light chains and a light chain constant region 1 (CLI) of an immunoglobulin. Additionally, as used herein, the term "Fc region mutant" refers to one prepared by substituting part of amino acid(s) of an Fc region or by combining Fc regions of different types.

The Fc region of immunoglobulin may be an entire Fc region constituting an antibody, a fragment thereof, or an Fc region mutant. Additionally, the Fc region includes a molecule in the form of a monomer or multimer, and may further include a hinge region of the heavy chain constant region. The Fc region mutant may be modified to prevent cleavage at the hinge region. Furthermore, the hinge sequence of the Fc may have a substitution in some amino acid sequences to reduce antibody-dependent cell-mediated cytotoxicity (ADCC) or complement-dependent cytotoxicity (CDC). In addition, part of the amino acid sequence of the Fc hinge sequence may be substituted to inhibit the rearrangement of the Fab region, lysine residue at the C-terminus of the Fc may be removed.

Preferably, the Fc region of immunoglobulin may be any one of IgG1, IgG2, IgG3, IgG4 and IgD Fc regions; or a hybrid Fc, which is a combination thereof. Further, the hybrid Fc may include an IgG4 region and an IgD region. Further, the hybrid Fc region may include part of the hinge sequence and CH2 of an IgD Fc, and CH2 and CH3 sequences of IgG4 Fc.

In addition, the Fc fragment of the present invention may be in the form of wild-type glycosylated chain, more glycosylated chain than the wild-type, less glycosylated chain than the wild-type, or deglycosylated chain. The increase, decrease, or removal of glycosylated chain may be performed by a conventional method known in the art, such as a chemical method, an enzymatic method, and a genetic engineering method using microorganisms.

Preferably, the immunoglobulin Fc region may be represented by an amino acid sequence selected from SEQ ID NOs: 24 to 28.

Dual Function Protein

The dual function protein may include a biologically active protein, an Fc region of an immunoglobulin and an FGF21 mutant protein, linked in this order from the N-terminus to the C-terminus. Further, the dual function protein may include an FGF21 mutant protein, an Fc region of an immunoglobulin and a biologically active protein, linked in this order from the N-terminus to the C-terminus. Preferably, the dual function protein may include a GLP-1 mutant protein, an Fc region of an immunoglobulin and an FGF21 mutant protein, linked in this order from the N-terminus to the C-terminus. Further, the dual function protein may include an FGF21 mutant protein, an Fc region of an immunoglobulin and a GLP-1 mutant protein, linked in this order from the N-terminus to the C-terminus.

Linker

Additionally; the dual function protein may further include a linker.

The dual function protein may be in the form, in which FGF21 mutant protein is directly connected to the N-terminus or C-terminus of the immunoglobulin Fc region, or the FGF21 mutant protein is connected to the immunoglobulin Fc region via a linker.

In such case, the linker may be connected to the N-terminus, C-terminus, or a free radical of the Fc fragment, and also, may be connected to the N-terminus, C-terminus, it) or a free radical of the FGF21 mutant protein. When the linker is a peptide linker, the connection may occur in any region. For example, the linker may be connected to the C-terminus of the immunoglobulin Fc region and the N-terminus of the FGF21 mutant protein to form a fusion protein of the immunoglobulin Fc region and the FGF21 mutant protein. Furthermore, the dual function protein of the present invention may be in the form, in which a biologically active protein is linked to the N-terminus of the Fc region of immunoglobulin of the fusion protein.

When the linker and Fc are separately expressed and then connected, the linker may be a crosslinking agent known in the art. Examples of the crosslinking agent may include 1,1-bis(diazoacetyl)-2-phenylethane, glutaraldehyde, imidoesters including N-hydroxysuccinimide ester such as 4-azidosalicylic acid and disuccinimidyl esters such as 3,3'-dithiobis(succinimidylpropionate), and bifunctional maleimides such as bis-N-maleimido-1,8-octane, but are not limited thereto.

Further, the linker may be a peptide. Preferably, the linker may be a peptide consisting of 10 to 30 amino acid residues.

Furthermore, alanine may additionally be attached to the end of linker. Preferably, the linker may be a peptide having an amino acid sequence represented by any one of SEQ ID NOs: 2 to 5.

The dual function protein may be in a form in which a dimer or multimer of FGF21 mutant proteins, in which one or more FGF21 mutant proteins linked together, is connected to an immunoglobulin Fc region. Additionally, the dual function protein may be in a form of a dimer or multimer in which two or more immunoglobulin Fc regions are linked, wherein the immunoglobulin Fc regions have the FGF21 mutant protein connected thereto.

Mammalian Host Cell

The mammalian host cell may be any animal cell capable of expressing a recombinant dual function protein, preferably an animal cell which allows easy isolation of a targeted transformed cell. Specifically, the mammalian host cells may be immortal hybridoma cells, NS/0 myeloma cells, 293 cells, Chinese hamster ovary cells (CHO cells), HeLa cells, CAP cells (human amniotic fluid-derived cells), or COS cells.

Dextran Sulfate

As a result of applying the protease inhibitor to the cell culture of a dual function protein of the present invention, the effect of preventing the clipping phenomenon of the dual function protein by the protease derived from the host cell was insufficient.

The dextran sulfate may have a weight average molecular weight of 20 to 5,000 kDa. Specifically, the dextran sulfate may have a weight average molecular weight of 200 to 5,000 kDa.

In addition, the culture medium may contain the dextran sulfate at a concentration of 0.01 to 10 g/L. Specifically, the culture medium may contain the dextran sulfate at a concentration of 0.1 to 10 g/L, or 0.1 to 1 g/L.

Culture

The culturing may comprise a step for primary-culturing the mammalian host cell at 34 to 37° C. in a culture medium supplemented with dextran sulfate; and a step for secondary-culturing the primary-cultured medium at 28 to 33° C.

Specifically, the primary-culturing may be conducted for 24 to 144 hours. Also, the secondary-culturing may be conducted at 31 to 33° C.

The dual function protein is a polypeptide in which GLP-1 and FGF21 variants, biologically active proteins, are fused to the Fc region of an immunoglobulin, and is expressed in an intact form when produced by animal cell culture, and shows activity as a composition for preventing or treating hepatitis, hepatic fibrosis, and hepatic cirrhosis.

MODE FOR THE INVENTION

Hereinafter, exemplary embodiments of the present invention will be described in detail with reference to the examples. However, these examples according to the present invention can be modified in many different forms and the scope of the present invention should not be construed as limited to the examples set forth herein.

EXAMPLES

Preparation Example 1. Preparation of Host Cells for Expression of Dual Function Proteins 1-1: Preparation of Expression Vectors for Expression of Dual Function Proteins The position, sequence information, target and expected effect of each mutation introduced into the FGF21 protein are listed in Table 1 below (in Table 1, N refers to glycosylated asparagine (N)). Further, FGF21 mutant proteins including the mutations described in Table 1 are listed in Table 2 below.

TABLE 1

| Sequence | Position | Original sequence | Mutated sequence | Target | Expected effect |
|---|---|---|---|---|---|
| EIRP (SEQ ID NO: 53) | 98-101 | LLLE (SEQ ID NO: 57) | EIRP (SEQ ID NO: 53) | Substitution with FGF19 sequence | Improvement of stability and pharmacokinetics |
| TGLEAV (SEQ ID NO: 54) | 170-174 | GPSQG (SEQ ID NO: 58) | TGLEAV (SEQ ID NO: 54) | Substitution with FGF19 sequence | Improvement of pharmacokinetics |
| TGLEAN (SEQ ID NO: 55) | 170-174 | GPSQG (SEQ ID NO: 58) | TGLEAN (SEQ ID NO: 55) | Substitution with FGF19 sequence, and addition of N-glycosylation | Improvement of pharmacokinetics |
| G170N | 170 | G | N | Point mutation, and addition of N-glycosylation | Improvement of pharmacokinetics |

TABLE 1-continued

| Sequence | Position | Original sequence | Mutated sequence | Target | Expected effect |
|---|---|---|---|---|---|
| G174N | 174 | G | N | Point mutation, and addition of N-glycosylation | Improvement of pharmacokinetics |
| A180E | 180 | A | E | Point mutation | Improvement of pharmacokinetics |

TABLE 2

| SEQ ID NO | Sequence of FGF21 mutant protein |
|---|---|
| 6 | FGF21 (EIRP) |
| 7 | FGF21 (TGLEAV) |
| 8 | FGF21 (TGLEAN) |
| 9 | FGF21 (G170N) |
| 10 | FGF21 (G174N) |
| 11 | FGF21 (EIRP, TGLEAV) |
| 12 | FGF21 (EIRP, TGLEAN) |
| 13 | FGF21 (EIRP, G170N) |
| 14 | FGF21 (EIRP, G174N) |
| 15 | FGF21 (EIRP, A180E) |
| 16 | FGF21 (TGLEAV, A180E) |
| 17 | FGF21 (TGLEAN, A180E) |
| 18 | FGF21 (G170N, A180E) |
| 19 | FGF21 (G174N, A180E) |
| 20 | FGF21 (EIRP, TGLEAV, A180E) |
| 21 | FGF21 (EIRP, TGLEAN, A180E) |
| 22 | FGF21 (EIRP, G170N, A180E) |
| 23 | FGF21 (EIRP, G174N, A180E) |

The GLP-1 mutant protein sequences are shown in Table 3 below, and the Fc fusion GLP-1 mutant protein sequences are shown in Table 4.

TABLE 3

| SEQ ID NO | Sequence of GLP-1 mutant protein |
|---|---|
| 30 | GLP-1 (A2G) |
| 31 | GLP-1 (GE) |
| 32 | GLP-1 (GG) |
| 33 | GLP-1 (GEG) |

TABLE 4

| SEQ ID NO | Fc fusion GLP-1 mutant protein |
|---|---|
| 34 | DFD52: GLP1(A2G)-HyFc5 |
| 35 | DFD53: GLP1(A2G)-HyFc40 |
| 36 | DFD54: GLP1(GE)-HyFc5 |
| 37 | DFD55: GLP1(GE)-HyFc40 |
| 38 | DFD56: GLP1(GG)-HyFc5 |
| 39 | DFD57: GLP1(GG)-HyFc40 |
| 40 | DFD58: GLP1(GEG)-HyFc5 |
| 41 | DFD59: GLP1(GEG)-HyFc40 |

In Table 4, HyFc5 represents SEQ ID NO: 27 and HyFc40 represents SEQ ID NO: 28.

Further, the sequences of the dual function proteins including the GLP-1 mutant proteins and FGF21 mutant proteins are listed in Table 5 below. Each dual function protein contains a GLP-1 mutant protein, an Fc region of an immunoglobulin, a linker and an FGF21 mutant protein connected in this order from the N-terminus to C-terminus.

TABLE 5

| SEQ ID NO | Material code | Sequence of GLP-1 mutant protein | Fusion carrier | Linker sequence | Changes in FGF21 sequence |
|---|---|---|---|---|---|
| 43 | DFD23 | GLP-1 (A2G) | hyFc40 (SEQ ID NO: 28) | GS3 (SEQ ID NO: 4) | FGF21 (EIRP, TGLEAV) |
| 44 | DFD24 | GLP-1 (GE) | hyFc5 (SEQ ID NO: 27) | GS3 (SEQ ID NO: 4) | FGF21 (EIRP, TGLEAV) |
| 45 | DFD25 | GLP-1 (GE) | hyFc40 (SEQ ID NO: 28) | GS3 (SEQ ID NO: 4) | FGF21 (EIRP, TGLEAV) |
| 46 | DFD26 | GLP-1 (GG) | hyFc5 (SEQ ID NO: 27) | GS3 (SEQ ID NO: 4) | FGF21 (EIRP, TGLEAV) |
| 47 | DFD27 | GLP-1 (GG) | hyFc40 (SEQ ID NO: 28) | GS3 (SEQ ID NO: 4) | FGF21 (EIRP, TGLEAV) |
| 48 | DFD28 | GLP-1 (GEG) | hyFc5 (SEQ ID NO: 27) | GS3 (SEQ ID NO: 4) | FGF21 (EIRP, TGLEAV) |
| 49 | DFD29 | GLP-1 (GEG) | hyFc40 (SEQ ID NO: 28) | GS3 (SEQ ID NO: 4) | FGF21 (EIRP, TGLEAV) |
| 50 | DFD69 | GLP-1 (GEG) | hyFc40 (SEQ ID NO: 28) | GS3 (SEQ ID NO: 4) | FGF21 (EIRP, TGLEAV, A180E) |
| 51 | DFD112 | GLP-1 (GEG) | hyFc40 (SEQ ID NO: 28) | GS3 (SEQ ID NO: 4) | FGF21 (EIRP, TGLEAN, A180E) |
| 52 | DFD114 | GLP-1 (GEG) | hyFc40 (SEQ ID NO: 28) | GS3 (SEQ ID NO: 4) | FGF21 (EIRP, G170N, A180E) |

Specifically, the nucleotide sequences encoding each of the dual function proteins were synthesized after consulting with Bioneer Corporation (Korea) based on the amino acid sequence of each protein. NheI and NotI restriction enzyme sequences were added to the 5' terminus and terminus of the nucleotide sequences encoding each of the dual function proteins and an initiation codon for protein translation and a leader sequence (SEQ ID NO: 56, MDAMLR-GLCCVLLLCGAVFVSPSHA) enabling secretion of the expressed protein to the outside of a cell were inserted next to the restriction enzyme sequence at the 5' terminus. A termination codon was inserted to next to the nucleotide sequence, which encodes each of the FGF21 mutant proteins. The nucleotide sequence encoding each of the dual function proteins was cloned into a pTrans-empty expression vector by using the two restriction enzymes NheI and NotI. The pTrans-empty expression vector, which has a CMV promoter, a pUC-derived replication origin, an SV40-derived replication origin and an ampicillin-resistance gene, was purchased from CEVEC Pharmaceuticals (Germany).

1-2: Construction of Plasmid DNA for Expression of Dual Function Proteins

E. coli was transformed with each of the expression vectors constructed in Preparation Example 1-1 to obtain a large quantity of plasmid DNA to be used for expression. E. coli cells, with cell walls weakened through heat shock, were transformed with each expression vector, and the transformants were plated out on an LB plate to obtain colonies. The colonies thus obtained were inoculated into LB media, cultured at 37° C. for 16 hours, and each E. coli culture containing each expression vector was obtained in a volume of 100 mL. The E. coli thereafter obtained was centrifuged to remove the culture medium, and then P1, P2, P3 solutions (QIAGEN, Cat No.:12963) were added to break the cell walls, thereby obtaining a DNA suspension in which proteins and DNA were separated. Plasmid DNA was purified from the DNA suspension thus Obtained by using a Qiagen DNA purification column. The eluted plasmid DNA was identified by agarose gel electrophoresis, and the concentrations and purities were measured using a nanodrop device (Thermo Scientific, Nanodrop Lite). The DNA thus obtained was used for expression.

1-3: Production of Transformed Host Cells for Expression of Dual Function Proteins CHO DG44 cells (Chinese hamster ovary cells) were transformed with each plasmid DNA isolated in Preparation Example 1-2 using FreeStyleMAX (Invitrogen, Cat. No. 16447-100). The transformed Chinese hamster ovary cells were inoculated into a medium (CD OptiCHO, Gibco, Cat. No. 12681-011), and cultured in an incubator under the condition of 8% $CO_2$ and 37° C., to select and culture surviving cells with passages repeatedly. The selected cells were finally selected as a single clone by limiting dilution in a 96-well plate.

Experimental Example 1. Suspension Culture for Expression of Dual Function Proteins, and Decomposition Phenomenon The CHO cell line transformed with the material code DFD112 (SEQ ID NO: 51) of Preparation Example 1-3 was suspension-cultured in CD OptiCHO medium supplemented with 8 mM GlutaMAX (working volume 30 ml/125 ml flask, 37° C., 8% $CO_2$, 120 rpm). Thereafter, the culture supernatants were stored at three different storage temperatures (37° C., 4° C., or −20° C.) for 3 days, and then the degrees of proteolysis phenomenon were evaluated by SDS-PAGE (4-12% Bis-Tris, non-reducing condition) analysis of the culture supernatant. The results of SDS-PAGE analysis are shown in FIGS. 1 and 2.

As shown in FIG. 1, it was found that proteins (85 to 110 kDa) smaller than target proteins were expressed along with the target proteins which were unclipped (intact) during cell culture for producing dual function proteins.

As shown in FIG. 2, the culture supernatants stored at 4° C. and −20° C. had less small-sized proteins in which the dual function proteins were clipped as compared to the culture supernatant stored at 37° C. Accordingly, it was found that the decomposition phenomenon of the dual function protein was caused by the proteases secreted from the host cell present in the culture supernatant.

Experimental Example 2. Detection of Protease Inhibitors Involved in Dual Function Protein Decomposition In order to examine the category of the proteases involved in the decomposition of the dual function proteins identified in Experimental Example 1, the culture supernatants of Experimental Example 1 was added with various protease inhibitors, and treated for 3 days at 37° C., which were then subjected to SDS-PAGE analysis. The protease inhibitors used herein are shown in Table 6, and SDS-PAGE analysis results are shown in FIG. 3.

TABLE 6

| Protease inhibitors | Treatment concentration |
| --- | --- |
| Culture supernatant (control) | N/A |
| 4-(2-Aminoethyl)benzenesulfonyl fluoride (AEBSF) | 1 mM |
| Antipain | 0.1 mM |
| Bestatin | 0.04 mM |
| E-64 | 0.01 mM |
| EDTA disodium salt | 1 mM |
| N-Ethylmaleimide | 1 mM |
| Leupeptin | 0.1 mM |
| Pepstatin | 1.46 mM |
| Phosphoramidon | 0.01 mM |
| Benzamidine-HCl | 4 mM |
| $ZnCl_2$ | 10 mM |
| Aprotinin | 0.0008 mM |

As shown in FIG. 3, it was found that the decomposition phenomenon of the dual function protein was reduced in the culture supernatants treated with proteases inhibitors related to serine protease such as AEBSF, Antipain, Leupeptin, Benzamidine-HCl and Aprotin. Accordingly, it was found that the decomposition phenomenon of the dual function protein was caused by the proteases derived from the host cell.

Example 1. Dextran Sulfate Treatment

In order to inhibit the clipping phenomenon occurring during cell culture of the dual function proteins, the transformed CHO cell line of Preparation Example 1-3 was suspension-cultured in CD Dynamis medium (Gibco, cat. No. A2661501) supplemented with 6 mM glutamine for 7 days (working volume 30 mL/125 mL flask, 37° C., 8% $CO_2$, 120 rpm). As for the suspension culture, dextran sulfate (weight average molecular weight: 1.6 kDa or 500 kDa) was added to the culture medium at a concentration of 200 mg/L, and the culture was conducted at 32° C. by a low temperature-conversion and fed-batch culture method. Thereafter, the culture supernatant was analyzed by SDS-PAGE (4-12% Bis-Tris, non-reducing condition), and the result of the SDS-PAGE analysis and a schematic diagram thereof are shown in FIG. 4. In FIG. 4, w/o and Lane 1 are controls, 500 kDa and Lane 2 are the culture supernatants treated with 500 kDa dextran sulfate, and 1.6 kDa and Lane 3 are the culture supernatants treated with 1.6 kDa dextran sulfate.

As shown in FIG. 4, it was found that the clipping phenomenon of the dual function protein was effectively inhibited when dextran sulfate having a weight average molecular weight of 500 kDa was added to the culture medium.

Example 2. Effect of Dextran Sulfate According to Molecular Weight

The effective concentration range of dextran sulfate to be added, whose protective effect against the clipping phenomenon of the dual function protein during cell culture was identified in Example 1, was examined.

Specifically, the culture was conducted under the same condition as Example 1 except for adjusting the weight average molecular weight (1.6 kDa, 8 kDa or 200 kDa) and the concentration (100 mg/L, 200 mg/L or 500 mg/L) of the added dextran sulfate. Thereafter, the culture supernatant was analyzed by SDS-PAGE (4-12% Bis-Tris, non-reducing condition), and the result of SDS-PAGE analysis and its graph are shown in FIG. 5.

As shown in FIG. 5, the clipping phenomenon of the dual function protein was significantly reduced when the dextran sulfate having a molecular weight of 200 kDa or more was added to the culture medium at a concentration of 100 to 500 mg/L.

Example 3. Evaluation of Culture Conditions for Prevention of Dual Function Protein Decomposition The culture conditions for maximizing the effect of preventing the clipping of dual function proteins by dextran sulfate identified in Examples 1 and 2 were examined.

Specifically, the culture was conducted under the same condition as Example 1 except that dextran sulfate of 500 kDa was added at a concentration of 0 mg/L to 1,000 mg/L. Herein, the experiment group in which the culture temperature was changed to 32° C. on Day 4 of culture was included (see Table 7 below). Then, the culture supernatant was analyzed by SDS-PAGE (4-12% Bis-Tris, non-reducing condition), and the result of SDS-PAGE analysis and its graph are shown in FIG. 6.

TABLE 7

| Lane | Concentration of the added Dextran sulfate | Culture condition |
|---|---|---|
| 1 | 0 | Culture at 32° C. for 3 days after culture at 37° C. for 4 days |
| 2 | | Culture at 37° C. for 7 days |
| 3 | 200 mg/L | Culture at 32° C. for 3 days after culture at 37° C. for 4 days |
| 4 | | Culture at 37° C. for 7 days |
| 5 | 600 mg/L | Culture at 32° C. for 3 days after culture at 37° C. for 4 days |
| 6 | | Culture at 37° C. for 7 days |
| 7 | 1,000 mg/L | Culture at 32° C. for 3 days after culture at 37° C. for 4 days |
| 8 | | Culture at 37° C. for 7 days |

As shown in FIG. 6, it was found that the culture supernatants of the culture with the treatment of dextran sulfate having a weight average molecular weight of 500 kDa showed significantly reduced clipping phenomenon of the dual function protein as compared to the culture supernatants of the culture without the treatment of dextran sulfate. Also, it was found that when the temperature was changed during the culture, the clipping phenomenon of the dual function protein was more effectively inhibited.

The invention claimed is:

1. A method for producing a recombinant dual function protein from a mammalian host cell transformed with an expression vector containing cDNA encoding the recombinant dual function protein, the method comprising culturing the mammalian host cell in a culture medium supplemented with dextran sulfate, wherein the dual function protein comprises a fibroblast growth factor 21 (FGF21) mutant protein; a biologically active protein, or a biologically active mutant or biologically active fragment thereof; and an Fc region of an immunoglobulin, wherein the FGF21 mutant protein comprises one mutation selected from the group consisting of the following mutations (a), (b), (c), (d), and (e):
  (a) a substitution of amino acids at positions 98 to 101 from the N-terminus of a wild-type FGF21 protein with the amino acid sequence of EIRP (SEQ ID NO: 53);
  (b) a substitution of amino acids at positions 170 to 174 from the N-terminus of a wild-type FGF21 protein with the amino acid sequence of TGLEAV (SEQ ID NO: 54);
  (c) a substitution of amino acids at positions 170 to 174 from the N-terminus of a wild-type FGF21 protein with the amino acid sequence of TGLEAN (SEQ ID NO: 55);
  (d) a substitution of an amino acid at position 174 from the N-terminus of a wild-type FGF21 protein with the amino acid N; and
  (e) a combination of the (a) and (b), a combination of the (a) and (c), or a combination of the (a) and (d), and
  wherein the wild-type FGF21 protein in (a), (b), (c), and (d) comprises the amino acid sequence of SEQ ID NO: 1.

2. The method according to claim 1, wherein the biologically active protein is one selected from the group consisting of insulin, C-peptide, leptin, glucagon, gastrin, gastric inhibitory polypeptide (GIP), amylin, calcitonin, cholecystokinin, peptide YY, neuropeptide Y, bone morphogenetic protein-6 (BMP-6), bone morphogenetic protein-9 (BMP-9), oxyntomodulin, oxytocin, glucagon-like peptide-1 (GLP-1), glucagon-like peptide-2 (GLP-2), irisin, fibronectin type III domain-containing protein 5 (FNDC5), apelin, adiponectin, C1q and tumor necrosis factor related protein (CTRP family), resistin, visfatin, omentin, retinol binding protein-4 (RBP-4), glicentin, angiopoietin, interleukin-22 (IL-22), exendin-4 and growth hormone.

3. The method according to claim 1, wherein the dual function protein comprises the biologically active protein, the Fc region of the immunoglobulin and the FGF21 mutant protein, connected in this order from the N-terminus to the C-terminus of the dual function protein.

4. The method according to claim 1, wherein the dextran sulfate has a weight average molecular weight of 20 to 5,000 kDa.

5. The method according to claim 1, wherein the culture medium contains the dextran sulfate at a concentration of 0.01 to 10 g/L.

6. The method according to claim 1, wherein the culturing comprises:
  a step for primary-culturing the mammalian host cell at 34 to 37° C. in a culture medium supplemented with dextran sulfate; and
  a step for secondary-culturing the primary-cultured medium at 28 to 33° C.

7. The method of claim 6, wherein the primary-culturing is conducted for 24 to 144 hours.

8. The method of claim 6, wherein the secondary-culturing is conducted at 31 to 33° C.

* * * * *

SEQUENCE LISTING

<160> NUMBER OF SEQ ID NOS: 58

<210> SEQ ID NO 1
<211> LENGTH: 181
<212> TYPE: PRT
<213> ORGANISM: human FGF21

<400> SEQUENCE: 1

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 2
<211> LENGTH: 30
<212> TYPE: PRT
<213> ORGANISM: Artificial Sequence
<220> FEATURE:
<223> OTHER INFORMATION: linker

<400> SEQUENCE: 2

```
Ala Lys Ala Thr Thr Ala Pro Ala Thr Thr Arg Asn Thr Gly Arg Gly
1               5                   10                  15

Gly Glu Glu Lys Lys Glu Lys Glu Lys Glu Glu Gln Glu
            20                  25                  30
```

<210> SEQ ID NO 3
<211> LENGTH: 17
<212> TYPE: PRT
<213> ORGANISM: Artificial Sequence
<220> FEATURE:
<223> OTHER INFORMATION: linker

<400> SEQUENCE: 3

```
Ala Lys Ala Thr Thr Ala Pro Ala Thr Thr Arg Asn Thr Gly Arg Gly
1               5                   10                  15

Gly
```

<210> SEQ ID NO 4
<211> LENGTH: 15
<212> TYPE: PRT
<213> ORGANISM: Artificial Sequence
<220> FEATURE:
<223> OTHER INFORMATION: linker

<400> SEQUENCE: 4

```
Gly Gly Gly Gly Ser Gly Gly Gly Gly Ser Gly Gly Gly Gly Ser
1               5                   10                  15
```

<210> SEQ ID NO 5
<211> LENGTH: 16
<212> TYPE: PRT
<213> ORGANISM: Artificial Sequence
<220> FEATURE:
<223> OTHER INFORMATION: linker

<400> SEQUENCE: 5

```
Gly Gly Gly Gly Ser Gly Gly Gly Gly Ser Gly Gly Gly Gly Ser Ala
1               5                   10                  15
```

<210> SEQ ID NO 6
<211> LENGTH: 181
<212> TYPE: PRT
<213> ORGANISM: Artificial Sequence
<220> FEATURE:
<223> OTHER INFORMATION: FGF21 variant

<400> SEQUENCE: 6

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
            100                 105                 110

Gly Leu Pro Leu His Leu Pro Gly Asn Lys Ser Pro His Arg Asp Pro
```

-continued

```
                115                 120                 125

Ala Pro Arg Gly Pro Ala Arg Phe Leu Pro Leu Pro Gly Leu Pro Pro
            130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 7
<211> LENGTH: 182
<212> TYPE: PRT
<213> ORGANISM: Artificial Sequence
<220> FEATURE:
<223> OTHER INFORMATION: FGF21 variant

<400> SEQUENCE: 7

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Val Arg
                165                 170                 175

Ser Pro Ser Tyr Ala Ser
            180

<210> SEQ ID NO 8
<211> LENGTH: 182
<212> TYPE: PRT
<213> ORGANISM: Artificial Sequence
<220> FEATURE:
<223> OTHER INFORMATION: FGF21 variant

<400> SEQUENCE: 8

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45
```

-continued

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Asn Arg
                165                 170                 175

Ser Pro Ser Tyr Ala Ser
            180

<210> SEQ ID NO 9
<211> LENGTH: 181
<212> TYPE: PRT
<213> ORGANISM: Artificial Sequence
<220> FEATURE:
<223> OTHER INFORMATION: FGF21 variant

<400> SEQUENCE: 9

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Asn Pro Ser Gln Gly Arg Ser
                165                 170                 175

Pro Ser Tyr Ala Ser
        180

<210> SEQ ID NO 10
<211> LENGTH: 181
<212> TYPE: PRT
<213> ORGANISM: Artificial Sequence
<220> FEATURE:

<223> OTHER INFORMATION: FGF21 variant

<400> SEQUENCE: 10

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Asn Arg Ser
                165                 170                 175

Pro Ser Tyr Ala Ser
            180

<210> SEQ ID NO 11
<211> LENGTH: 182
<212> TYPE: PRT
<213> ORGANISM: Artificial Sequence
<220> FEATURE:
<223> OTHER INFORMATION: FGF21 variant

<400> SEQUENCE: 11

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

```
Gly Ser Ser Asp Pro Leu Ser Met Val Thr Gly Leu Glu Ala Val Arg
            165                 170                 175

Ser Pro Ser Tyr Ala Ser
            180

<210> SEQ ID NO 12
<211> LENGTH: 182
<212> TYPE: PRT
<213> ORGANISM: Artificial Sequence
<220> FEATURE:
<223> OTHER INFORMATION: FGF21 variant

<400> SEQUENCE: 12

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Asn Arg
                165                 170                 175

Ser Pro Ser Tyr Ala Ser
            180

<210> SEQ ID NO 13
<211> LENGTH: 181
<212> TYPE: PRT
<213> ORGANISM: Artificial Sequence
<220> FEATURE:
<223> OTHER INFORMATION: FGF21 variant

<400> SEQUENCE: 13

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
```

```
            85                  90                  95
Glu Glu Ile Arg Pro Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Asn Pro Ser Gln Gly Arg Ser
                165                 170                 175

Pro Ser Tyr Ala Ser
            180

<210> SEQ ID NO 14
<211> LENGTH: 181
<212> TYPE: PRT
<213> ORGANISM: Artificial Sequence
<220> FEATURE:
<223> OTHER INFORMATION: FGF21 variant

<400> SEQUENCE: 14

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Asn Arg Ser
                165                 170                 175

Pro Ser Tyr Ala Ser
            180

<210> SEQ ID NO 15
<211> LENGTH: 181
<212> TYPE: PRT
<213> ORGANISM: Artificial Sequence
<220> FEATURE:
<223> OTHER INFORMATION: FGF21 variant

<400> SEQUENCE: 15

His Pro Ile Pro Asp Ser Ser Pro Leu Leu Gln Phe Gly Gly Gln Val
1               5                   10                  15
```

```
Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
         35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Glu Ile Arg Pro Asp Gly Tyr Asn Val Tyr Gln Ser Glu Ala His
             100                 105                 110

Gly Leu Pro Leu His Leu Pro Gly Asn Lys Ser Pro His Arg Asp Pro
         115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Glu Ser
            180

<210> SEQ ID NO 16
<211> LENGTH: 182
<212> TYPE: PRT
<213> ORGANISM: Artificial Sequence
<220> FEATURE:
<223> OTHER INFORMATION: FGF21 variant

<400> SEQUENCE: 16

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
         35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
             100                 105                 110

Gly Leu Pro Leu His Leu Pro Gly Asn Lys Ser Pro His Arg Asp Pro
         115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Val Arg
                165                 170                 175

Ser Pro Ser Tyr Glu Ser
            180
```

<210> SEQ ID NO 17
<211> LENGTH: 182
<212> TYPE: PRT
<213> ORGANISM: Artificial Sequence
<220> FEATURE:
<223> OTHER INFORMATION: FGF21 variant

<400> SEQUENCE: 17

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Asn Arg
                165                 170                 175

Ser Pro Ser Tyr Glu Ser
            180
```

<210> SEQ ID NO 18
<211> LENGTH: 181
<212> TYPE: PRT
<213> ORGANISM: Artificial Sequence
<220> FEATURE:
<223> OTHER INFORMATION: FGF21 variant

<400> SEQUENCE: 18

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125
```

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Asn Pro Ser Gln Gly Arg Ser
                165                 170                 175

Pro Ser Tyr Glu Ser
            180

<210> SEQ ID NO 19
<211> LENGTH: 181
<212> TYPE: PRT
<213> ORGANISM: Artificial Sequence
<220> FEATURE:
<223> OTHER INFORMATION: FGF21 variant

<400> SEQUENCE: 19

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Asn Arg Ser
                165                 170                 175

Pro Ser Tyr Glu Ser
            180

<210> SEQ ID NO 20
<211> LENGTH: 182
<212> TYPE: PRT
<213> ORGANISM: Artificial Sequence
<220> FEATURE:
<223> OTHER INFORMATION: FGF21 variant

<400> SEQUENCE: 20

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln

```
                    50                  55                  60
Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Glu Ile Arg Pro Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Val Arg
                165                 170                 175

Ser Pro Ser Tyr Glu Ser
            180

<210> SEQ ID NO 21
<211> LENGTH: 182
<212> TYPE: PRT
<213> ORGANISM: Artificial Sequence
<220> FEATURE:
<223> OTHER INFORMATION: FGF21 variant

<400> SEQUENCE: 21

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Glu Ile Arg Pro Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Asn Arg
                165                 170                 175

Ser Pro Ser Tyr Glu Ser
            180

<210> SEQ ID NO 22
<211> LENGTH: 181
<212> TYPE: PRT
<213> ORGANISM: Artificial Sequence
<220> FEATURE:
<223> OTHER INFORMATION: FGF21 variant
```

<400> SEQUENCE: 22

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Asn Pro Ser Gln Gly Arg Ser
                165                 170                 175

Pro Ser Tyr Glu Ser
            180
```

<210> SEQ ID NO 23
<211> LENGTH: 181
<212> TYPE: PRT
<213> ORGANISM: Artificial Sequence
<220> FEATURE:
<223> OTHER INFORMATION: FGF21 variant

<400> SEQUENCE: 23

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Glu Ile Arg Pro Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160
```

Gly Ser Ser Asp Pro Leu Ser Met Val Gly Pro Ser Gln Asn Arg Ser
            165                 170                 175

Pro Ser Tyr Glu Ser
            180

<210> SEQ ID NO 24
<211> LENGTH: 229
<212> TYPE: PRT
<213> ORGANISM: Artificial Sequence
<220> FEATURE:
<223> OTHER INFORMATION: Human IgG4 Fc

<400> SEQUENCE: 24

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 25
<211> LENGTH: 228
<212> TYPE: PRT
<213> ORGANISM: Artificial Sequence
<220> FEATURE:
<223> OTHER INFORMATION: Human IgG4 Fc variant

<400> SEQUENCE: 25

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225

<210> SEQ ID NO 26
<211> LENGTH: 223
<212> TYPE: PRT
<213> ORGANISM: Artificial Sequence
<220> FEATURE:
<223> OTHER INFORMATION: Hybrid Fc variant

<400> SEQUENCE: 26

Glu Thr Lys Thr Pro Glu Cys Pro Ser His Thr Gln Pro Leu Gly Val
 1               5                  10                  15

Phe Leu Phe Pro Pro Lys Pro Lys Asp Thr Leu Met Ile Ser Arg Thr
                 20                  25                  30

Pro Glu Val Thr Cys Val Val Asp Val Ser Gln Glu Asp Pro Glu
             35                  40                  45

Val Gln Phe Asn Trp Tyr Val Asp Gly Val Glu Val His Asn Ala Lys
 50                  55                  60

Thr Lys Pro Arg Glu Glu Gln Phe Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Gln Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Gly Lys
    210                 215                 220

<210> SEQ ID NO 27
<211> LENGTH: 245
<212> TYPE: PRT
<213> ORGANISM: Artificial Sequence
<220> FEATURE:
<223> OTHER INFORMATION: hybrid Fc5

<400> SEQUENCE: 27

Arg Asn Thr Gly Arg Gly Gly Glu Glu Lys Lys Glu Lys Glu Lys Glu
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Glu Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Leu Gly Lys
                245

<210> SEQ ID NO 28
<211> LENGTH: 233
<212> TYPE: PRT
<213> ORGANISM: Artificial Sequence
<220> FEATURE:
<223> OTHER INFORMATION: hybrid Fc40

<400> SEQUENCE: 28

Glu Lys Glu Lys Glu Glu Gln Glu Glu Arg Glu Thr Lys Thr Pro Glu

```
             1               5                  10                 15
            Cys Pro Ser His Thr Gln Pro Leu Gly Val Phe Leu Phe Pro Pro Lys
                           20                 25                 30

Pro Lys Asp Thr Leu Met Ile Ser Arg Thr Pro Glu Val Thr Cys Val
                           35                 40                 45

Val Val Asp Val Ser Gln Glu Asp Pro Glu Val Gln Phe Asn Trp Tyr
             50                 55                 60

Val Asp Gly Val Glu Val His Asn Ala Lys Thr Lys Pro Arg Glu Glu
             65                 70                 75                 80

Gln Phe Asn Ser Thr Tyr Arg Val Val Ser Val Leu Thr Val Leu His
                           85                 90                 95

Gln Asp Trp Leu Asn Gly Lys Glu Tyr Lys Cys Lys Val Ser Asn Lys
                           100                105                110

Gly Leu Pro Ser Ser Ile Glu Lys Thr Ile Ser Lys Ala Lys Gly Gln
                           115                120                125

Pro Arg Glu Pro Gln Val Tyr Thr Leu Pro Pro Ser Gln Glu Glu Met
                           130                135                140

Thr Lys Asn Gln Val Ser Leu Thr Cys Leu Val Lys Gly Phe Tyr Pro
            145                150                155                160

Ser Asp Ile Ala Val Glu Trp Glu Ser Asn Gly Gln Pro Glu Asn Asn
                           165                170                175

Tyr Lys Thr Thr Pro Pro Val Leu Asp Ser Asp Gly Ser Phe Phe Leu
                           180                185                190

Tyr Ser Arg Leu Thr Val Asp Lys Ser Arg Trp Gln Glu Gly Asn Val
                           195                200                205

Phe Ser Cys Ser Val Met His Glu Ala Leu His Asn His Tyr Thr Gln
            210                215                220

Lys Ser Leu Ser Leu Ser Leu Gly Lys
            225                230

<210> SEQ ID NO 29
            <211> LENGTH: 31
            <212> TYPE: PRT
            <213> ORGANISM: Artificial Sequence
            <220> FEATURE:
            <223> OTHER INFORMATION: GLP-1

<400> SEQUENCE: 29

His Ala Glu Gly Thr Phe Thr Ser Asp Val Ser Ser Tyr Leu Glu Gly
            1               5                  10                 15

Gln Ala Ala Lys Glu Phe Ile Ala Trp Leu Val Lys Gly Arg Gly
                           20                 25                 30

<210> SEQ ID NO 30
            <211> LENGTH: 31
            <212> TYPE: PRT
            <213> ORGANISM: Artificial Sequence
            <220> FEATURE:
            <223> OTHER INFORMATION: GLP-1 variant

<400> SEQUENCE: 30

His Gly Glu Gly Thr Phe Thr Ser Asp Val Ser Ser Tyr Leu Glu Gly
            1               5                  10                 15

Gln Ala Ala Lys Glu Phe Ile Ala Trp Leu Val Lys Gly Arg Gly
                           20                 25                 30

<210> SEQ ID NO 31
            <211> LENGTH: 31
```

```
<212> TYPE: PRT
<213> ORGANISM: Artificial Sequence
<220> FEATURE:
<223> OTHER INFORMATION: GLP-1 variant

<400> SEQUENCE: 31

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly
            20                  25                  30

<210> SEQ ID NO 32
<211> LENGTH: 31
<212> TYPE: PRT
<213> ORGANISM: Artificial Sequence
<220> FEATURE:
<223> OTHER INFORMATION: GLP-1 variant

<400> SEQUENCE: 32

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly
            20                  25                  30

<210> SEQ ID NO 33
<211> LENGTH: 31
<212> TYPE: PRT
<213> ORGANISM: Artificial Sequence
<220> FEATURE:
<223> OTHER INFORMATION: GLP-1 variant

<400> SEQUENCE: 33

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

<210> SEQ ID NO 34
<211> LENGTH: 276
<212> TYPE: PRT
<213> ORGANISM: Artificial Sequence
<220> FEATURE:
<223> OTHER INFORMATION: GLP-1 variant connected to hybrid Fc5

<400> SEQUENCE: 34

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Arg
            20                  25                  30

Asn Thr Gly Arg Gly Gly Glu Glu Lys Lys Lys Glu Lys Glu Lys Glu
        35                  40                  45

Glu Gln Glu Glu Arg Glu Thr Lys Thr Pro Glu Cys Pro Ser His Thr
    50                  55                  60

Gln Pro Leu Gly Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125
```

```
Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
                260                 265                 270

Ser Leu Gly Lys
        275

<210> SEQ ID NO 35
<211> LENGTH: 264
<212> TYPE: PRT
<213> ORGANISM: Artificial Sequence
<220> FEATURE:
<223> OTHER INFORMATION: GLP-1 variant connected to hybrid Fc40

<400> SEQUENCE: 35

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Glu
            20                  25                  30

Lys Glu Lys Glu Glu Gln Glu Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
    130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205
```

```
Lys Thr Thr Pro Pro Val Leu Asp Ser Asp Gly Ser Phe Phe Leu Tyr
    210             215                 220

Ser Arg Leu Thr Val Asp Lys Ser Arg Trp Gln Glu Gly Asn Val Phe
225             230                 235                 240

Ser Cys Ser Val Met His Glu Ala Leu His Asn His Tyr Thr Gln Lys
                245                 250                 255

Ser Leu Ser Leu Ser Leu Gly Lys
                260

<210> SEQ ID NO 36
<211> LENGTH: 276
<212> TYPE: PRT
<213> ORGANISM: Artificial Sequence
<220> FEATURE:
<223> OTHER INFORMATION: GLP-1 variant connected to hybrid Fc5

<400> SEQUENCE: 36

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Arg
                20                  25                  30

Asn Thr Gly Arg Gly Gly Glu Glu Lys Lys Glu Lys Glu Lys Glu Lys
            35                  40                  45

Glu Gln Glu Glu Arg Glu Thr Lys Thr Pro Glu Cys Pro Ser His Thr
50                  55                  60

Gln Pro Leu Gly Val Phe Leu Phe Pro Pro Lys Pro Lys Asp Thr Leu
65                  70                  75                  80

Met Ile Ser Arg Thr Pro Glu Val Thr Cys Val Val Asp Val Ser
                85                  90                  95

Gln Glu Asp Pro Glu Val Gln Phe Asn Trp Tyr Val Asp Gly Val Glu
                100                 105                 110

Val His Asn Ala Lys Thr Lys Pro Arg Glu Glu Gln Phe Asn Ser Thr
            115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
            195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
                260                 265                 270

Ser Leu Gly Lys
            275

<210> SEQ ID NO 37
<211> LENGTH: 264
```

```
<212> TYPE: PRT
<213> ORGANISM: Artificial Sequence
<220> FEATURE:
<223> OTHER INFORMATION: GLP-1 variant connected to hybrid Fc40

<400> SEQUENCE: 37

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Glu
            20                  25                  30

Lys Glu Lys Glu Glu Gln Glu Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
    130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys
            260

<210> SEQ ID NO 38
<211> LENGTH: 276
<212> TYPE: PRT
<213> ORGANISM: Artificial Sequence
<220> FEATURE:
<223> OTHER INFORMATION: GLP-1 variant connected to hybrid Fc5

<400> SEQUENCE: 38

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Arg
            20                  25                  30

Asn Thr Gly Arg Gly Gly Glu Glu Lys Lys Lys Glu Lys Glu Lys Glu
        35                  40                  45

Glu Gln Glu Glu Arg Glu Thr Lys Thr Pro Glu Cys Pro Ser His Thr
    50                  55                  60
```

Gln Pro Leu Gly Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys
        275

<210> SEQ ID NO 39
<211> LENGTH: 264
<212> TYPE: PRT
<213> ORGANISM: Artificial Sequence
<220> FEATURE:
<223> OTHER INFORMATION: GLP-1 variant connected to hybrid Fc40

<400> SEQUENCE: 39

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Glu
            20                  25                  30

Lys Glu Lys Glu Glu Gln Glu Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
            195                 200                 205

Lys Thr Thr Pro Pro Val Leu Asp Ser Asp Gly Ser Phe Phe Leu Tyr
210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
            245                 250                 255

Ser Leu Ser Leu Ser Leu Gly Lys
            260

<210> SEQ ID NO 40
<211> LENGTH: 276
<212> TYPE: PRT
<213> ORGANISM: Artificial Sequence
<220> FEATURE:
<223> OTHER INFORMATION: GLP-1 variant connected to hybrid Fc5

<400> SEQUENCE: 40

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Arg
                20                  25                  30

Asn Thr Gly Arg Gly Gly Glu Lys Lys Lys Glu Lys Glu Lys Glu Glu
            35                  40                  45

Glu Gln Glu Glu Arg Glu Thr Lys Thr Pro Glu Cys Pro Ser His Thr
50                  55                  60

Gln Pro Leu Gly Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
            115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
            195                 200                 205

Glu Trp Glu Ser Asn Gly Gln Pro Glu Asn Asn Tyr Lys Thr Thr Pro
        210                 215                 220

Pro Val Leu Asp Ser Asp Gly Ser Phe Phe Leu Tyr Ser Arg Leu Thr
225                 230                 235                 240

-continued

Val Asp Lys Ser Arg Trp Gln Glu Gly Asn Val Phe Ser Cys Ser Val
            245                 250                 255

Met His Glu Ala Leu His Asn His Tyr Thr Gln Lys Ser Leu Ser Leu
        260                 265                 270

Ser Leu Gly Lys
        275

<210> SEQ ID NO 41
<211> LENGTH: 264
<212> TYPE: PRT
<213> ORGANISM: Artificial Sequence
<220> FEATURE:
<223> OTHER INFORMATION: GLP-1 variant connected to hybrid Fc40

<400> SEQUENCE: 41

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Glu
            20                  25                  30

Lys Glu Lys Glu Glu Gln Glu Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
    130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys
            260

<210> SEQ ID NO 42
<211> LENGTH: 275
<212> TYPE: PRT
<213> ORGANISM: Artificial Sequence
<220> FEATURE:
<223> OTHER INFORMATION: Dulaglutide

<400> SEQUENCE: 42

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Ala Glu
        35                  40                  45

Ser Lys Tyr Gly Pro Pro Cys Pro Pro Cys Pro Ala Pro Glu Ala Ala
50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly
        275

<210> SEQ ID NO 43
<211> LENGTH: 461
<212> TYPE: PRT
<213> ORGANISM: Artificial Sequence
<220> FEATURE:
<223> OTHER INFORMATION: GLP1(A2G)-HyFc40-GS3-FGF21(EIRP, TGLEAV)

<400> SEQUENCE: 43

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Glu
            20                  25                  30

Lys Glu Lys Glu Glu Gln Glu Arg Glu Thr Lys Thr Pro Glu Cys
        35                  40                  45

Pro Ser His Thr Gln Pro Leu Gly Val Phe Leu Phe Pro Pro Lys Pro
50                  55                  60

Lys Asp Thr Leu Met Ile Ser Arg Thr Pro Glu Val Thr Cys Val Val

```
                65                  70                  75                  80
Val Asp Val Ser Gln Glu Asp Pro Glu Val Gln Phe Asn Trp Tyr Val
                        85                  90                  95

Asp Gly Val Glu Val His Asn Ala Lys Thr Lys Pro Arg Glu Glu Gln
                    100                 105                 110

Phe Asn Ser Thr Tyr Arg Val Val Ser Val Leu Thr Val Leu His Gln
                    115                 120                 125

Asp Trp Leu Asn Gly Lys Glu Tyr Lys Cys Lys Val Ser Asn Lys Gly
            130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
                180                 185                 190

Asp Ile Ala Val Glu Trp Glu Ser Asn Gly Gln Pro Glu Asn Asn Tyr
            195                 200                 205

Lys Thr Thr Pro Pro Val Leu Asp Ser Asp Gly Ser Phe Phe Leu Tyr
210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys Gly Gly Gly Gly Ser Gly Gly Gly
                260                 265                 270

Gly Ser Gly Gly Gly Ser His Pro Ile Pro Asp Ser Ser Pro Leu
            275                 280                 285

Leu Gln Phe Gly Gly Gln Val Arg Gln Arg Tyr Leu Tyr Thr Asp Asp
            290                 295                 300

Ala Gln Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
                340                 345                 350

Leu Cys Gln Arg Pro Asp Gly Ala Leu Tyr Gly Ser Leu His Phe Asp
            355                 360                 365

Pro Glu Ala Cys Ser Phe Arg Glu Glu Ile Arg Pro Asp Gly Tyr Asn
370                 375                 380

Val Tyr Gln Ser Glu Ala His Gly Leu Pro Leu His Leu Pro Gly Asn
385                 390                 395                 400

Lys Ser Pro His Arg Asp Pro Ala Pro Arg Gly Pro Ala Arg Phe Leu
                405                 410                 415

Pro Leu Pro Gly Leu Pro Pro Ala Leu Pro Glu Pro Pro Gly Ile Leu
            420                 425                 430

Ala Pro Gln Pro Pro Asp Val Gly Ser Ser Asp Pro Leu Ser Met Val
            435                 440                 445

Thr Gly Leu Glu Ala Val Arg Ser Pro Ser Tyr Ala Ser
450                 455                 460

<210> SEQ ID NO 44
<211> LENGTH: 473
<212> TYPE: PRT
<213> ORGANISM: Artificial Sequence
```

<220> FEATURE:
<223> OTHER INFORMATION: GLP1(GE)-HyFc5-GS3-FGF21(EIRP, TGLEAV)

<400> SEQUENCE: 44

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Arg
            20                  25                  30

Asn Thr Gly Arg Gly Gly Glu Lys Lys Glu Lys Glu Lys Glu
        35                  40                  45

Glu Gln Glu Glu Arg Glu Thr Lys Thr Pro Glu Cys Pro Ser His Thr
    50                  55                  60

Gln Pro Leu Gly Val Phe Leu Phe Pro Pro Lys Pro Lys Asp Thr Leu
65              70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys Gly Gly Gly Ser Gly Gly Gly Ser Gly Gly
        275                 280                 285

Gly Gly Ser His Pro Ile Pro Asp Ser Ser Pro Leu Leu Gln Phe Gly
    290                 295                 300

Gly Gln Val Arg Gln Arg Tyr Leu Tyr Thr Asp Asp Ala Gln Gln Thr
305                 310                 315                 320

Glu Ala His Leu Glu Ile Arg Glu Asp Gly Thr Val Gly Gly Ala Ala
                325                 330                 335

Asp Gln Ser Pro Glu Ser Leu Leu Gln Leu Lys Ala Leu Lys Pro Gly
            340                 345                 350

Val Ile Gln Ile Leu Gly Val Lys Thr Ser Arg Phe Leu Cys Gln Arg
        355                 360                 365

Pro Asp Gly Ala Leu Tyr Gly Ser Leu His Phe Asp Pro Glu Ala Cys
    370                 375                 380

Ser Phe Arg Glu Glu Ile Arg Pro Asp Gly Tyr Asn Val Tyr Gln Ser
385                 390                 395                 400

Glu Ala His Gly Leu Pro Leu His Leu Pro Gly Asn Lys Ser Pro His
            405                 410                 415

Arg Asp Pro Ala Pro Arg Gly Pro Ala Arg Phe Leu Pro Leu Pro Gly
            420                 425                 430

Leu Pro Pro Ala Leu Pro Glu Pro Pro Gly Ile Leu Ala Pro Gln Pro
            435                 440                 445

Pro Asp Val Gly Ser Ser Asp Pro Leu Ser Met Val Thr Gly Leu Glu
450                 455                 460

Ala Val Arg Ser Pro Ser Tyr Ala Ser
465                 470

<210> SEQ ID NO 45
<211> LENGTH: 461
<212> TYPE: PRT
<213> ORGANISM: Artificial Sequence
<220> FEATURE:
<223> OTHER INFORMATION: GLP1(GE)-HyFc40-GS3-FGF21(EIRP, TGLEAV)

<400> SEQUENCE: 45

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Glu
            20                  25                  30

Lys Glu Lys Glu Glu Gln Glu Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
    130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys Gly Gly Gly Gly Ser Gly Gly Gly
            260                 265                 270

Gly Ser Gly Gly Gly Gly Ser His Pro Ile Pro Asp Ser Ser Pro Leu
        275                 280                 285

-continued

Leu Gln Phe Gly Gly Gln Val Arg Gln Arg Tyr Leu Tyr Thr Asp Asp
        290                 295                 300

Ala Gln Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
                340                 345                 350

Leu Cys Gln Arg Pro Asp Gly Ala Leu Tyr Gly Ser Leu His Phe Asp
            355                 360                 365

Pro Glu Ala Cys Ser Phe Arg Glu Glu Ile Arg Pro Asp Gly Tyr Asn
        370                 375                 380

Val Tyr Gln Ser Glu Ala His Gly Leu Pro Leu His Leu Pro Gly Asn
385                 390                 395                 400

Lys Ser Pro His Arg Asp Pro Ala Pro Arg Gly Pro Ala Arg Phe Leu
                405                 410                 415

Pro Leu Pro Gly Leu Pro Pro Ala Leu Pro Glu Pro Pro Gly Ile Leu
                420                 425                 430

Ala Pro Gln Pro Pro Asp Val Gly Ser Ser Asp Pro Leu Ser Met Val
            435                 440                 445

Thr Gly Leu Glu Ala Val Arg Ser Pro Ser Tyr Ala Ser
450                 455                 460

<210> SEQ ID NO 46
<211> LENGTH: 473
<212> TYPE: PRT
<213> ORGANISM: Artificial Sequence
<220> FEATURE:
<223> OTHER INFORMATION: GLP1(GG)-HyFc5-GS3-FGF21(EIRP, TGLEAV)

<400> SEQUENCE: 46

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Arg
                20                  25                  30

Asn Thr Gly Arg Gly Gly Glu Glu Lys Lys Lys Glu Lys Glu Lys Glu
            35                  40                  45

Glu Gln Glu Glu Arg Glu Thr Lys Thr Pro Glu Cys Pro Ser His Thr
        50                  55                  60

Gln Pro Leu Gly Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
                100                 105                 110

Val His Asn Ala Lys Thr Lys Pro Arg Glu Glu Gln Phe Asn Ser Thr
            115                 120                 125

Tyr Arg Val Val Ser Val Leu Thr Val Leu His Gln Asp Trp Leu Asn
        130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
            195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
            245                 250                 255

Met His Glu Ala Leu His Asn His Tyr Thr Gln Lys Ser Leu Ser Leu
            260                 265                 270

Ser Leu Gly Lys Gly Gly Gly Gly Ser Gly Gly Gly Ser Gly Gly
            275                 280                 285

Gly Gly Ser His Pro Ile Pro Asp Ser Ser Pro Leu Leu Gln Phe Gly
        290                 295                 300

Gly Gln Val Arg Gln Arg Tyr Leu Tyr Thr Asp Asp Ala Gln Gln Thr
305                 310                 315                 320

Glu Ala His Leu Glu Ile Arg Glu Asp Gly Thr Val Gly Gly Ala Ala
            325                 330                 335

Asp Gln Ser Pro Glu Ser Leu Leu Gln Leu Lys Ala Leu Lys Pro Gly
            340                 345                 350

Val Ile Gln Ile Leu Gly Val Lys Thr Ser Arg Phe Leu Cys Gln Arg
            355                 360                 365

Pro Asp Gly Ala Leu Tyr Gly Ser Leu His Phe Asp Pro Glu Ala Cys
        370                 375                 380

Ser Phe Arg Glu Glu Ile Arg Pro Asp Gly Tyr Asn Val Tyr Gln Ser
385                 390                 395                 400

Glu Ala His Gly Leu Pro Leu His Leu Pro Gly Asn Lys Ser Pro His
            405                 410                 415

Arg Asp Pro Ala Pro Arg Gly Pro Ala Arg Phe Leu Pro Leu Pro Gly
            420                 425                 430

Leu Pro Pro Ala Leu Pro Glu Pro Pro Gly Ile Leu Ala Pro Gln Pro
            435                 440                 445

Pro Asp Val Gly Ser Ser Asp Pro Leu Ser Met Val Thr Gly Leu Glu
        450                 455                 460

Ala Val Arg Ser Pro Ser Tyr Ala Ser
465                 470

<210> SEQ ID NO 47
<211> LENGTH: 461
<212> TYPE: PRT
<213> ORGANISM: Artificial Sequence
<220> FEATURE:
<223> OTHER INFORMATION: GLP1(GG)-HyFc40-GS3-FGF21(EIRP, TGLEAV)

<400> SEQUENCE: 47

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Glu
            20                  25                  30

Lys Glu Lys Glu Glu Gln Glu Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
             85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
            115                 120                 125

Asp Trp Leu Asn Gly Lys Glu Tyr Lys Cys Lys Val Ser Asn Lys Gly
130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
            195                 200                 205

Lys Thr Thr Pro Pro Val Leu Asp Ser Asp Gly Ser Phe Phe Leu Tyr
210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys Gly Gly Gly Ser Gly Gly Gly
            260                 265                 270

Gly Ser Gly Gly Gly Ser His Pro Ile Pro Asp Ser Ser Pro Leu
            275                 280                 285

Leu Gln Phe Gly Gly Gln Val Arg Gln Arg Tyr Leu Tyr Thr Asp Asp
290                 295                 300

Ala Gln Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
            340                 345                 350

Leu Cys Gln Arg Pro Asp Gly Ala Leu Tyr Gly Ser Leu His Phe Asp
            355                 360                 365

Pro Glu Ala Cys Ser Phe Arg Glu Glu Ile Arg Pro Asp Gly Tyr Asn
370                 375                 380

Val Tyr Gln Ser Glu Ala His Gly Leu Pro Leu His Leu Pro Gly Asn
385                 390                 395                 400

Lys Ser Pro His Arg Asp Pro Ala Pro Arg Gly Pro Ala Arg Phe Leu
                405                 410                 415

Pro Leu Pro Gly Leu Pro Pro Ala Leu Pro Glu Pro Pro Gly Ile Leu
            420                 425                 430

Ala Pro Gln Pro Pro Asp Val Gly Ser Ser Asp Pro Leu Ser Met Val
            435                 440                 445

Thr Gly Leu Glu Ala Val Arg Ser Pro Ser Tyr Ala Ser
450                 455                 460

<210> SEQ ID NO 48
<211> LENGTH: 473
<212> TYPE: PRT
<213> ORGANISM: Artificial Sequence
<220> FEATURE:

<223> OTHER INFORMATION: GLP1(GEG)-HyFc5-GS3-FGF21(EIRP, TGLEAV)

<400> SEQUENCE: 48

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Arg
            20                  25                  30

Asn Thr Gly Arg Gly Gly Glu Lys Lys Glu Lys Glu Lys Glu
        35                  40                  45

Glu Gln Glu Glu Arg Glu Thr Lys Thr Pro Glu Cys Pro Ser His Thr
    50                  55                  60

Gln Pro Leu Gly Val Phe Leu Phe Pro Pro Lys Pro Lys Asp Thr Leu
65                  70                  75                  80

Met Ile Ser Arg Thr Pro Glu Val Thr Cys Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys Gly Gly Gly Ser Gly Gly Gly Ser Gly Gly
        275                 280                 285

Gly Gly Ser His Pro Ile Pro Asp Ser Ser Pro Leu Leu Gln Phe Gly
    290                 295                 300

Gly Gln Val Arg Gln Arg Tyr Leu Tyr Thr Asp Asp Ala Gln Thr
305                 310                 315                 320

Glu Ala His Leu Glu Ile Arg Glu Asp Gly Thr Val Gly Gly Ala Ala
                325                 330                 335

Asp Gln Ser Pro Glu Ser Leu Leu Gln Leu Lys Ala Leu Lys Pro Gly
            340                 345                 350

Val Ile Gln Ile Leu Gly Val Lys Thr Ser Arg Phe Leu Cys Gln Arg
        355                 360                 365

Pro Asp Gly Ala Leu Tyr Gly Ser Leu His Phe Asp Pro Glu Ala Cys
    370                 375                 380

Ser Phe Arg Glu Glu Ile Arg Pro Asp Gly Tyr Asn Val Tyr Gln Ser
385                 390                 395                 400
```

```
Glu Ala His Gly Leu Pro Leu His Leu Pro Gly Asn Lys Ser Pro His
            405                 410                 415

Arg Asp Pro Ala Pro Arg Gly Pro Ala Arg Phe Leu Pro Leu Pro Gly
        420                 425                 430

Leu Pro Pro Ala Leu Pro Glu Pro Pro Gly Ile Leu Ala Pro Gln Pro
            435                 440                 445

Pro Asp Val Gly Ser Ser Asp Pro Leu Ser Met Val Thr Gly Leu Glu
    450                 455                 460

Ala Val Arg Ser Pro Ser Tyr Ala Ser
465                 470

<210> SEQ ID NO 49
<211> LENGTH: 461
<212> TYPE: PRT
<213> ORGANISM: Artificial Sequence
<220> FEATURE:
<223> OTHER INFORMATION: GLP1(GEG)-HyFc40-GS3-FGF21(EIRP, TGLEAV)

<400> SEQUENCE: 49

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Glu
            20                  25                  30

Lys Glu Lys Glu Glu Gln Glu Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
    130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys Gly Gly Gly Gly Ser Gly Gly Gly
            260                 265                 270

Gly Ser Gly Gly Gly Gly Ser His Pro Ile Pro Asp Ser Ser Pro Leu
        275                 280                 285
```

```
Leu Gln Phe Gly Gly Gln Val Arg Gln Arg Tyr Leu Tyr Thr Asp Asp
        290                 295                 300

Ala Gln Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
            340                 345                 350

Leu Cys Gln Arg Pro Asp Gly Ala Leu Tyr Gly Ser Leu His Phe Asp
        355                 360                 365

Pro Glu Ala Cys Ser Phe Arg Glu Glu Ile Arg Pro Asp Gly Tyr Asn
370                 375                 380

Val Tyr Gln Ser Glu Ala His Gly Leu Pro Leu His Leu Pro Gly Asn
385                 390                 395                 400

Lys Ser Pro His Arg Asp Pro Ala Pro Arg Gly Pro Ala Arg Phe Leu
                405                 410                 415

Pro Leu Pro Gly Leu Pro Pro Ala Leu Pro Glu Pro Pro Gly Ile Leu
            420                 425                 430

Ala Pro Gln Pro Pro Asp Val Gly Ser Ser Asp Pro Leu Ser Met Val
        435                 440                 445

Thr Gly Leu Glu Ala Val Arg Ser Pro Ser Tyr Ala Ser
450                 455                 460

<210> SEQ ID NO 50
<211> LENGTH: 461
<212> TYPE: PRT
<213> ORGANISM: Artificial Sequence
<220> FEATURE:
<223> OTHER INFORMATION: GLP1(GEG)-HyFc40-GS3-FGF21(EIRP, TGLEAV, A180E)

<400> SEQUENCE: 50

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Glu
            20                  25                  30

Lys Glu Lys Glu Glu Gln Glu Glu Arg Glu Thr Lys Thr Pro Glu Cys
        35                  40                  45

Pro Ser His Thr Gln Pro Leu Gly Val Phe Leu Phe Pro Pro Lys Pro
50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
            100                 105                 110

Phe Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Gly
130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
            180                 185                 190
```

```
Asp Ile Ala Val Glu Trp Glu Ser Asn Gly Gln Pro Glu Asn Asn Tyr
            195                 200                 205

Lys Thr Thr Pro Pro Val Leu Asp Ser Asp Gly Ser Phe Phe Leu Tyr
    210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
            245                 250                 255

Ser Leu Ser Leu Ser Leu Gly Lys Gly Gly Gly Ser Gly Gly Gly
        260                 265                 270

Gly Ser Gly Gly Gly Ser His Pro Ile Pro Asp Ser Ser Pro Leu
    275                 280                 285

Leu Gln Phe Gly Gly Gln Val Arg Gln Arg Tyr Leu Tyr Thr Asp Asp
    290                 295                 300

Ala Gln Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
            340                 345                 350

Leu Cys Gln Arg Pro Asp Gly Ala Leu Tyr Gly Ser Leu His Phe Asp
        355                 360                 365

Pro Glu Ala Cys Ser Phe Arg Glu Glu Ile Arg Pro Asp Gly Tyr Asn
    370                 375                 380

Val Tyr Gln Ser Glu Ala His Gly Leu Pro Leu His Leu Pro Gly Asn
385                 390                 395                 400

Lys Ser Pro His Arg Asp Pro Ala Pro Arg Gly Pro Ala Arg Phe Leu
                405                 410                 415

Pro Leu Pro Gly Leu Pro Pro Ala Leu Pro Glu Pro Pro Gly Ile Leu
            420                 425                 430

Ala Pro Gln Pro Pro Asp Val Gly Ser Ser Asp Pro Leu Ser Met Val
        435                 440                 445

Thr Gly Leu Glu Ala Val Arg Ser Pro Ser Tyr Glu Ser
    450                 455                 460

<210> SEQ ID NO 51
<211> LENGTH: 461
<212> TYPE: PRT
<213> ORGANISM: Artificial Sequence
<220> FEATURE:
<223> OTHER INFORMATION: GLP1(GEG)-HyFc40-GS3-FGF21(EIRP, TGLEAN, A180E)

<400> SEQUENCE: 51

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Glu
            20                  25                  30

Lys Lys Glu Glu Gln Glu Glu Arg Glu Thr Lys Thr Pro Glu Cys
        35                  40                  45

Pro Ser His Thr Gln Pro Leu Gly Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser Gln Glu Asp Pro Glu Val Gln Phe Asn Trp Tyr Val
                85                  90                  95
```

```
Asp Gly Val Glu Val His Asn Ala Lys Thr Lys Pro Arg Glu Gln
            100                 105                 110
Phe Asn Ser Thr Tyr Arg Val Val Ser Val Leu Thr Val Leu His Gln
        115                 120                 125
Asp Trp Leu Asn Gly Lys Glu Tyr Lys Cys Lys Val Ser Asn Lys Gly
    130                 135                 140
Leu Pro Ser Ser Ile Glu Lys Thr Ile Ser Lys Ala Lys Gly Gln Pro
145                 150                 155                 160
Arg Glu Pro Gln Val Tyr Thr Leu Pro Pro Ser Gln Glu Glu Met Thr
                165                 170                 175
Lys Asn Gln Val Ser Leu Thr Cys Leu Val Lys Gly Phe Tyr Pro Ser
            180                 185                 190
Asp Ile Ala Val Glu Trp Glu Ser Asn Gly Gln Pro Glu Asn Asn Tyr
        195                 200                 205
Lys Thr Thr Pro Pro Val Leu Asp Ser Asp Gly Ser Phe Phe Leu Tyr
    210                 215                 220
Ser Arg Leu Thr Val Asp Lys Ser Arg Trp Gln Glu Gly Asn Val Phe
225                 230                 235                 240
Ser Cys Ser Val Met His Glu Ala Leu His Asn His Tyr Thr Gln Lys
                245                 250                 255
Ser Leu Ser Leu Ser Leu Gly Lys Gly Gly Gly Gly Ser Gly Gly Gly
            260                 265                 270
Gly Ser Gly Gly Gly Ser His Pro Ile Pro Asp Ser Ser Pro Leu
        275                 280                 285
Leu Gln Phe Gly Gly Gln Val Arg Gln Arg Tyr Leu Tyr Thr Asp Asp
    290                 295                 300
Ala Gln Gln Thr Glu Ala His Leu Glu Ile Arg Glu Asp Gly Thr Val
305                 310                 315                 320
Gly Gly Ala Ala Asp Gln Ser Pro Glu Ser Leu Leu Gln Leu Lys Ala
                325                 330                 335
Leu Lys Pro Gly Val Ile Gln Ile Leu Gly Val Lys Thr Ser Arg Phe
            340                 345                 350
Leu Cys Gln Arg Pro Asp Gly Ala Leu Tyr Gly Ser Leu His Phe Asp
        355                 360                 365
Pro Glu Ala Cys Ser Phe Arg Glu Glu Ile Arg Pro Asp Gly Tyr Asn
    370                 375                 380
Val Tyr Gln Ser Glu Ala His Gly Leu Pro Leu His Leu Pro Gly Asn
385                 390                 395                 400
Lys Ser Pro His Arg Asp Pro Ala Pro Arg Gly Pro Ala Arg Phe Leu
                405                 410                 415
Pro Leu Pro Gly Leu Pro Pro Ala Leu Pro Glu Pro Pro Gly Ile Leu
            420                 425                 430
Ala Pro Gln Pro Pro Asp Val Gly Ser Ser Asp Pro Leu Ser Met Val
        435                 440                 445
Thr Gly Leu Glu Ala Asn Arg Ser Pro Ser Tyr Glu Ser
    450                 455                 460

<210> SEQ ID NO 52
<211> LENGTH: 460
<212> TYPE: PRT
<213> ORGANISM: Artificial Sequence
<220> FEATURE:
<223> OTHER INFORMATION: GLP1(GEG)-HyFc40-GS3-FGF21(EIRP, G170N, A180E)

<400> SEQUENCE: 52
```

-continued

```
His Gly Glu Gly Thr Phe Thr Ser Asp Val Ser Ser Tyr Leu Glu Glu
 1               5                  10                  15

Gln Ala Ala Lys Glu Phe Ile Ala Trp Leu Val Lys Gly Gly Gly Glu
                20                  25                  30

Lys Glu Lys Glu Glu Gln Glu Glu Arg Glu Thr Lys Thr Pro Glu Cys
                35                  40                  45

Pro Ser His Thr Gln Pro Leu Gly Val Phe Leu Phe Pro Pro Lys Pro
 50                  55                  60

Lys Asp Thr Leu Met Ile Ser Arg Thr Pro Glu Val Thr Cys Val Val
 65                  70                  75                  80

Val Asp Val Ser Gln Glu Asp Pro Glu Val Gln Phe Asn Trp Tyr Val
                85                  90                  95

Asp Gly Val Glu Val His Asn Ala Lys Thr Lys Pro Arg Glu Glu Gln
                100                 105                 110

Phe Asn Ser Thr Tyr Arg Val Val Ser Val Leu Thr Val Leu His Gln
                115                 120                 125

Asp Trp Leu Asn Gly Lys Glu Tyr Lys Cys Lys Val Ser Asn Lys Gly
                130                 135                 140

Leu Pro Ser Ser Ile Glu Lys Thr Ile Ser Lys Ala Lys Gly Gln Pro
145                 150                 155                 160

Arg Glu Pro Gln Val Tyr Thr Leu Pro Pro Ser Gln Glu Glu Met Thr
                165                 170                 175

Lys Asn Gln Val Ser Leu Thr Cys Leu Val Lys Gly Phe Tyr Pro Ser
                180                 185                 190

Asp Ile Ala Val Glu Trp Glu Ser Asn Gly Gln Pro Glu Asn Asn Tyr
                195                 200                 205

Lys Thr Thr Pro Pro Val Leu Asp Ser Asp Gly Ser Phe Phe Leu Tyr
                210                 215                 220

Ser Arg Leu Thr Val Asp Lys Ser Arg Trp Gln Glu Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Leu Gly Lys Gly Gly Gly Gly Ser Gly Gly Gly
                260                 265                 270

Gly Ser Gly Gly Gly Gly Ser His Pro Ile Pro Asp Ser Ser Pro Leu
                275                 280                 285

Leu Gln Phe Gly Gly Gln Val Arg Gln Arg Tyr Leu Tyr Thr Asp Asp
                290                 295                 300

Ala Gln Gln Thr Glu Ala His Leu Glu Ile Arg Glu Asp Gly Thr Val
305                 310                 315                 320

Gly Gly Ala Ala Asp Gln Ser Pro Glu Ser Leu Leu Gln Leu Lys Ala
                325                 330                 335

Leu Lys Pro Gly Val Ile Gln Ile Leu Gly Val Lys Thr Ser Arg Phe
                340                 345                 350

Leu Cys Gln Arg Pro Asp Gly Ala Leu Tyr Gly Ser Leu His Phe Asp
                355                 360                 365

Pro Glu Ala Cys Ser Phe Arg Glu Glu Ile Arg Pro Asp Gly Tyr Asn
                370                 375                 380

Val Tyr Gln Ser Glu Ala His Gly Leu Pro Leu His Leu Pro Gly Asn
385                 390                 395                 400

Lys Ser Pro His Arg Asp Pro Ala Pro Arg Gly Pro Ala Arg Phe Leu
                405                 410                 415

Pro Leu Pro Gly Leu Pro Pro Ala Leu Pro Glu Pro Pro Gly Ile Leu
```

```
                420                 425                 430
Ala Pro Gln Pro Pro Asp Val Gly Ser Ser Asp Pro Leu Ser Met Val
            435                 440                 445

Asn Pro Ser Gln Gly Arg Ser Pro Ser Tyr Glu Ser
    450                 455                 460

<210> SEQ ID NO 53
<211> LENGTH: 4
<212> TYPE: PRT
<213> ORGANISM: Artificial Sequence
<220> FEATURE:
<223> OTHER INFORMATION: FGF21 variant

<400> SEQUENCE: 53

Glu Ile Arg Pro
1

<210> SEQ ID NO 54
<211> LENGTH: 6
<212> TYPE: PRT
<213> ORGANISM: Artificial Sequence
<220> FEATURE:
<223> OTHER INFORMATION: FGF21 variant

<400> SEQUENCE: 54

Thr Gly Leu Glu Ala Val
1               5

<210> SEQ ID NO 55
<211> LENGTH: 6
<212> TYPE: PRT
<213> ORGANISM: Artificial Sequence
<220> FEATURE:
<223> OTHER INFORMATION: FGF21 variant

<400> SEQUENCE: 55

Thr Gly Leu Glu Ala Asn
1               5

<210> SEQ ID NO 56
<211> LENGTH: 25
<212> TYPE: PRT
<213> ORGANISM: Artificial Sequence
<220> FEATURE:
<223> OTHER INFORMATION: derived sequences

<400> SEQUENCE: 56

Met Asp Ala Met Leu Arg Gly Leu Cys Cys Val Leu Leu Leu Cys Gly
1               5                   10                  15

Ala Val Phe Val Ser Pro Ser His Ala
            20                  25

<210> SEQ ID NO 57
<211> LENGTH: 4
<212> TYPE: PRT
<213> ORGANISM: Artificial Sequence
<220> FEATURE:
<223> OTHER INFORMATION: synthetic construct

<400> SEQUENCE: 57

Leu Leu Leu Glu
1

<210> SEQ ID NO 58
<211> LENGTH: 5
```

```
<212> TYPE: PRT
<213> ORGANISM: Artificial Sequence
<220> FEATURE:
<223> OTHER INFORMATION: Synthetic construct

<400> SEQUENCE: 58

Gly Pro Ser Gln Gly
1               5
```